US006872809B2

(12) United States Patent
Inoue et al.

(10) Patent No.: US 6,872,809 B2
(45) Date of Patent: Mar. 29, 2005

(54) NUCLEOSIDE DERIVATIVES

(75) Inventors: Yoshihisa Inoue, Toyonaka (JP); Takehiko Wada, Toyonaka (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/311,048

(22) PCT Filed: Jun. 13, 2001

(86) PCT No.: PCT/JP01/05011

§ 371 (c)(1),
(2), (4) Date: Dec. 12, 2002

(87) PCT Pub. No.: WO01/96355

PCT Pub. Date: Dec. 20, 2001

(65) Prior Publication Data

US 2003/0208050 A1 Nov. 6, 2003

(51) Int. Cl.[7] .......................... C07G 3/00; C07H 21/02; C07H 21/04

(52) U.S. Cl. ....................... 536/4.1; 536/23.1; 536/25.3

(58) Field of Search ................................ 536/4.1, 23.1, 536/25.3

(56) References Cited

PUBLICATIONS

Takehiko Wada, et al., "Peptide Ribonucleic Acids (PRNA). 2. A Novel Strategy for Active Control of DNA Recognition through Borate Ester Formation," Journal of the American Chemical Society, 2000, vol. 122, No. 29, pp. 6900–6910.
Takehiko Wada, et al., "Conformational and Orientational Switching of Uridine Derivatives by Borates," Chemistry Letters 1998, pp. 1025–1026.

Takehiko Wada, et al., "Synthesis and properties of oligolysine and oligoglutamic acid derivatives containing nucleosides," Nucleic Acids Symposium Series No. 29, pp. 79–80, 1993.
Takehiko Wada, et al., "Synthesis and properties of polyamide derivatives containing nucleosides," Nucleic Acids Symposium Series No. 35, pp. 97–98, 1996.

(List continued on next page.)

*Primary Examiner*—Jezia Riley
(74) *Attorney, Agent, or Firm*—Knobbe, Martens, Olson & Bear LLP

(57) ABSTRACT

Novel nucleoside derivatives represented by the following general formula (1):

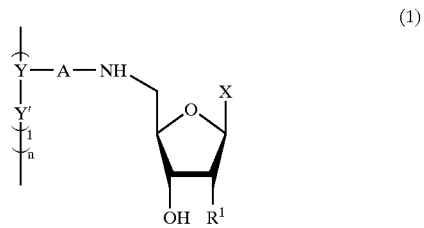

wherein X is(are) the same or different and each represents a pyrimidine or purine base or a derivative thereof, Y and Y' are the same or different and each represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a single bond or a carbonyl or thiocarbonyl group, 1 is an integer of 0 to 5, and n is an integer of 1 to 100.

27 Claims, 2 Drawing Sheets

PUBLICATIONS

Takehiko Wada, et al., "Synthesis and properties of oligo–ω–amino acids derivatives containing nucleosides," Nucleic Acids Symposium Series No. 34, pp. 189–190, 1995.

Hirofumi Sato, et al., "Synthesis and conformation control of peptide ribonucleic acid containing 5'–amino–5'–deoxyribopurinenucleosides," Nucleic Acids Symposium Series No. 44, pp. 211–212, 2000.

Jeewoo Lee, et al., "Methionyl Adenylate Analogues as Inhibitors of Methionyl–tRNA Synthetase," Bioorganic & Medicinal Chemistry Letters (1999), 9(10), pp. 1365–1370.

Kiyoshi Isono, et al., "Polyoxin Analogs. I. Synthesis of Aminoacyl Derivatives of 5'–Amino–5'–deoxyuridine," Chemical & Pharmaceutical Bulletin (1971), 19(3), pp. 505–512.

Rosario Herranz, et al., "Synthesis of 5'–N–(α–amino–β–mercaptoacyl)=amino–5'–deoxynucleosides as potential antiviral compounds," Chemical Abstracts, vol. 116, No. 1, Jan. 6, 1992.

Chi–Deu Chang; et al., "Analogues of S–adenosylhomocysteine as potential inhibitors of biological transmethylation. Synthesis of analogues with modifications at the 5'–thioether linkage," Journal of Medicinal Chemistry (1976), 19(5), pp. 684–691.

NUCLEOSIDE DERIVATIVES

This application is the U.S. National Phase under 35 U.S.C. §371 of International Application PCT/JP01/05011, filed Jun. 13, 2001, which claims priority to Japanese Patent Application No. 2000-177428, filed Jun. 13, 2000. The International Application was published under PCT Article 21(2) in a language other than English.

TECHNICAL FIELD

The present invention relates to novel nucleoside derivatives.

BACKGROUND ART

Nucleic acids are highly functional macromolecules involved in accumulation and transmission of genetic information in living organisms. Specific recognition between nucleic acids or between a nucleic acid and a protein plays an important role in the function expression and regulatory function of the nucleic acid. With the recent rapid advances in genetic engineering and molecular biology, the mechanisms of such function expression have further been understood on a molecular level. A number of genes causative of diseases have been identified and the mechanisms of onset of such diseases have gradually been elucidated. With a background of such results, gene therapy has attracted attention by which therapy a disease is treated on a gene level using, as a therapeutic agent, a molecule capable of specific recognition in a manner mimicking the mode of recognition of a naturally occurring nucleic acid. The techniques of gene therapy which have so far investigated include, among others, the "gene transfer method" comprising artificially introducing a defective or deficient gene sequence into a patient's gene, the "antisense method" comprising binding an antisense molecule to mRNA in a base (nucleotide)-specific manner to thereby inhibit the synthesis of a protein causative of a disease, and the "antigene method" comprising binding an antisense molecule to a DNA region coding for a pathogenic protein to thereby inhibit the stage of transcription.

The so-called antisense molecule to be used in the "antisense method" or "antigene method" among the above-mentioned methods is required to have a number of characteristics, among which the following are important: 1) high-level ability to recognize a nucleic acid base sequence, 2) high stability in the form of complexes, 3) high stability against biological substances, in particular enzymes, 4) high cell membrane permeability, 5) ability to specifically interact with nucleic acids, and 6) nontoxicity to living bodies.

At first, attempts were made to use natural oligonucleotides as antisense molecules. Although these comparatively meet the above requirements 1) and 2), they have a problem in that they cannot meet the requirement 3) but are instantly decomposed enzymatically by means of nuclease occurring in vivo, so that the desired results cannot be attained.

The antisense molecules so far reported include, among others, 1) derivatives resulting from modification around the phosphate bonding, 2) derivatives resulting from modification of the glycosyl bonding or a hydroxyl group(s) in the ribose sugar portion, 3) derivatives resulting from modification of the base portion, and 4) nucleic acid model molecules having a skeletal structure other than the sugar-phosphate skeleton. More specifically, there may be mentioned such derivatives 1) as phosphorothioate type oligonucleotides resulting from substitution of a sulfur atom for an oxygen atom of phosphoryl group in the phospho-diester bonding and, further, phosphorodithioate type, phosphoroamidate type, methylphosphonate type and methylphosphonothioate type oligonucleotides; such derivatives 2) as α-anomer type oligonucleotides with the base coordinated in the sugar moiety in a manner reverse to the β-glucosyl bonding, oligonucleotides resulting from conversion of the sugar 3'–5' phosphodiester bonding to the 2'–5' bonding using a ribonucleotide, and 2'-methoxy derivatives resulting from methyl etherification at the 2' position of ribose; such derivatives 3) as modified bases, for example 5-fluorouracil (5-FU) resulting from substitution of a fluorine atom at the 5 position of uracil, and fluorescent ethenoadenosine; such derivatives 4) as peptide nucleic acids (PNAs) having a peptide skeleton in place of the sugar-phosphate skeleton (O E. Uhlman, A. Peyman, Chem. Rev., 1990, 90, 544; O E. Uhlman, A, Peyman, G. Breipohl, D. W. Will, Angew. Chem. Int., Ed. Engl., 1998, 37, 2796, etc.).

The peptide nucleic acids (PNAs) so referred to herein are compounds which have attracted attention in view of such advantageous features as their base-specific recognizing ability, resistance to enzymolysis, very high affinity for nucleic acids owing to their having a neutral peptide chain as the main chain, and the possibility of arbitrary sequence being obtained in a simple and easy manner by the amide bond formation reaction. However, their excessively high affinity, for example their binding to targets, including mismatching, is rather disadvantageous, and drawbacks have also been reported, for example 15-mer or higher oligomers are nonspecifically adsorbed on intracellular proteins due to their having a hydrophobic peptide chain, or they are scarcely soluble in water.

Thus, there is room for improvement in antisense molecules, inclusive of PNAs.

DISCLOSURE OF INVENTION

Accordingly, it is an object of the present invention to provide novel nucleoside derivatives. More particularly, it is an object of the invention to provide novel nucleoside derivatives useful as antisense molecules owing to their having a property such that they are higher in affinity for nucleic acid base sequences than natural nucleic acids. and hardly subject to hydrolysis by enzymes occurring in vivo.

The present inventors constantly made intensive investigations in an attempt to solve the above problems and found, by chance, that the nucleoside derivatives; provided by the present invention are compounds useful as antisense molecules in the antisense method.

The present invention has been completed based on such finding.

Thus, the invention relates to nucleoside derivatives and methods of producing the same as shown below under paragraphs 1 to 18.

1. A nucleoside derivative represented by the general formula (1):

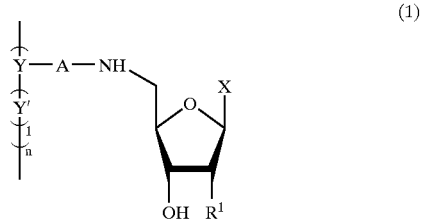

(1)

wherein X is(are) the same or different and each represents a pyrimidine or purine base or a derivative thereof, Y and Y' are the same or different and each represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a carbonyl or thiocarbonyl group, 1 is an integer of 0 to 5, and n is an integer of 1 to 100.

2. The nucleoside derivative according to claim 1, wherein, in general formula (1), X is uracil or a derivative thereof represented by the formula (2):

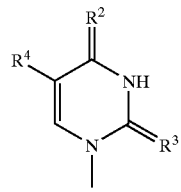

(2)

wherein $R^2$ and $R^3$ are the same or different and each represents an oxygen or sulfur atom, and $R^4$ represents a hydrogen or halogen atom or an alkyl, alkenyl or alkynyl group.

3. The nucleotide derivative according to claim 1, wherein, in general formula (1), X is at least one member selected from the group consisting of 5-fluorouracil, 5-bromouracil, 5-iodouracil, 2-thiouracil, 4-thiouracil, 2,4-dithiouracil, 5-methyluracil, 5-vinyluracil, 5-ethynyluracil, 5-fluorocytosine, 5-bromocytosine, 5-iodocytosine, 5-ethylcytosine, hypoxanthine, 8-fluoroguanine, 8-bromoguanine, 8-iodoguanine, 1,$N^6$-ethenoadenine, 8-fluoroadenine, 8-bromoadenine and 8-iodoadenine.

4. A nucleoside derivative represented by the general formula (1):

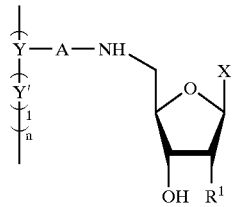

(1)

wherein X is(are) the same or different and each represents a pyrimidine or purine base or a derivative thereof, Y is a group represented by the formula (i):

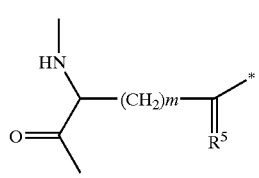

(i)

Wherein m is an integer of 1 to 3, $R^5$ represents an oxygen or sulfur atom, and * indicates the site of bonding to A in the nucleoside derivative represented by general formula (1);

Y' represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a single bond: 1 is an integer of 0 to 5, and n is an integer of 1 to 100.

6. The nucleoside derivative according to claim 1, wherein, in general formula (1), Y is a group represented by the formula (iii):

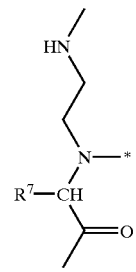

(iii)

wherein $R^7$ represents a hydrogen atom or a carboxymethyl, carboxyethyl, hydroxymethyl, aminobutyl or aminopropyl group, and * indicates the site of bonding to A in the nucleoside derivative represented by general formula (1): here, A represents a carbonyl or thiocarbonyl group.

7. A method for producing the nucleoside derivative of claim 4 which comprises the step 1 of producing a 5'-amino-nucleoside derivative by aminating the 5'-hydroxyl group of a nucleoside or a derivative thereof, the step 2 of producing an amino acid ω-pentachlorophenyl ester derivative by reacting an amino acid or a derivative thereof represented by the formula:

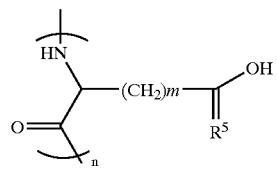

wherein $R^5$ represents an oxygen or sulfur atom, m is an integer of 1 to 3, and n is an integer of 1 to 100, with pentachlorophenyl trichloroacetate, and the step 3 of reacting the 5'-amino-nucleoside derivative and the amino acid ω-pentachlorophenyl ester derivative obtained in the step 1 and step 2, respectively, with each other for bonding them together.

9. A method for producing the nucleoside derivative oligomer or polymer (n=2 to 100) of claim 6 which comprises the step 1 of producing a nucleoside derivative monomer (n=1) by reacting a 5'-amino-nucleoside derivative with an amino acid or a derivative thereof protected at the N terminus and C terminus as represented by the formula:

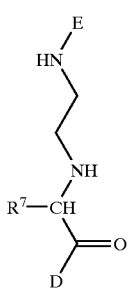

wherein R⁷ represents a hydrogen atom or a carboxymethyl, carboxyethyl, hydroxymethyl, aminobutyl or aminopropyl group, D represents a carboxyl-protecting group and E represents an amino-protecting group, the step 2 of deprotecting the C terminus of said monomer, the step 3 of deprotecting the N terminus of said monomer, the step 4 of reacting the C-terminus deprotection product obtained in step 2 with the N-terminus deprotection product obtained in step 3 in the manner of condensation, and the step of further repeating the steps 2 to 4 according to need.

15. A nucleoside derivative represented by the general formula (1):

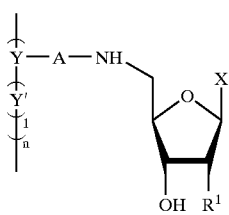

wherein X is(are) the same or different and each represents a pyrimidine or purine base or a derivative thereof, Y and Y' are the same or different and each represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, R¹ represents a hydrogen atom or a hydroxyl group, A represents a single bond 1 is an integer of 1 to 5, and n is an integer of 1 to 100.

16. The nucleoside derivative according to claim 15, wherein, in general formula (1), X is uracil or a derivative thereof represented by the formula (2):

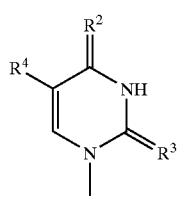

wherein R² and R³ are the same or different and each represents an oxygen or sulfur atom, and R⁴ represents a hydrogen or halogen atom or an alkyl, alkenyl or alkynyl group.

17. The nucleotide derivative according to claim 15, wherein, in general formula (1), X is at least one member selected from the group consisting of 5-fluorouracil, 5-bromouracil, 5-iodouracil, 2-thiouracil, 4-thiouracil, 2,4-dithiouracil, 5-methyluracil, 5-vinyluracil, 5-ethynyluracil, 5-fluorocytosine, 5-bromocytosine, 5-iodocytosine, 5-ethylcytosine, hypoxanthine, 8-fluoroguanine, 8-bromoguanine, 8-iodoguanine, 1,N⁶-ethenoadenine, 8-fluoroadenine, 8-bromoadenine and 8-iodoadenine.

18. The nucleoside derivative according to claim 15, wherein, in general formula (1), Y is a group represented by the formula (ii):

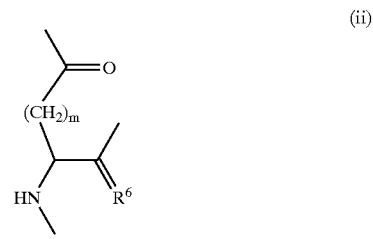

wherein m is an integer of 1 to 3, R⁶ represents an oxygen or sulfur atom, and * indicates the site of bonding to A in the nucleoside derivative represented by general formula (1).

19. An N-protected nucleoside derivative represented by the general formula:

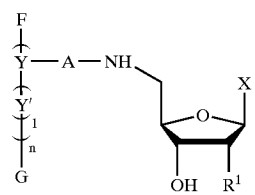

wherein X is(are) the same or different and each represents a pyrimidine or purine base or a derivative thereof, Y and Y' are the same or different and each represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, R¹ represents a hydrogen atom or a hydroxyl group, A represents a carbonyl or thiocarbonyl group, F represents a 9-fluorenylcarbonyl group, G represents a hydroxyl group or a benzyl ester group, 1 is an integer of 0 to 5, and n is 1.

20. An N-protected nucleoside derivative represented by the general formula:

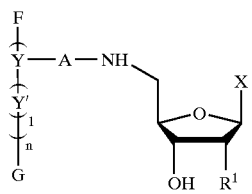

wherein X is(are) the same or different and each represents a pyrimidine or purine base or a derivative thereof, Y is a group represented by the formula (i):

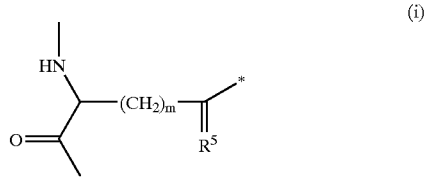

(i)

wherein m is an integer of 1 to 3, $R^5$ represents an oxygen or sulfur atom, and * indicates the site of bonding to A in the nucleoside derivative represented by general formula (1);
Y' represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid,
$R^1$ represents a hydrogen atom or a hydroxyl group, A represents a single bond, F represents a 9-fluorenylcarbonyl group, G represents a hydroxyl group or a benzyl ester group, 1 is an integer of 0 to 5, and n is 1.

21. An N-protected nucleoside derivative represented by the general formula:

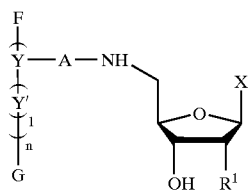

wherein X is(are) the same or different and each represents a pyrimidine or purine base or a derivative thereof, Y and Y' are the same or different and each represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a single bond, F represents a 9-fluorenylcarbonyl group, G represents a hydroxyl group or a benzyl ester group, and 1 is an integer of 1 to 5, and n is 1.

22. A solid phase method for producing oligo- or polynucleoside derivatives, wherein the N-protected nucleoside derivative according to any of claims 19, 20 and 21 is used as the starting monomer.

23. The solid phase method for producing oligo- or polynucleoside derivatives according to claim 22, which comprises the step of coupling the N-protected nucleoside derivative according to any of claims 19, 20 and 21 to a solid phase, the step of eliminating the N-protecting group from the solid phase-bound nucleoside derivative, and the step of coupling, to said nucleoside derivative, the N-protected nucleoside derivative according to any of claims 19, 20 and 21.

24. The use of the N-protected nucleoside derivative according to claim 19 as a starting material in the production of nucleoside derivatives represented by the general formula:

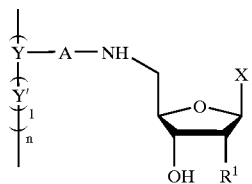

wherein X is(are) the same or different and each represents a pyrimidine or purine base or a derivative thereof, Y and Y' are the same or different and each represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a carbonyl or thiocarbonyl group, 1 is an integer of 0 to 5, and n is an integer of 2 to 100.

25. An use of the N-protected nucleoside derivative according to claim 20 as a starting material in the production of nucleoside derivatives represented by the general formula:

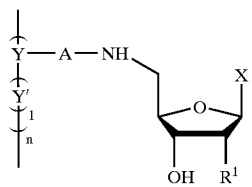

wherein X is(are) the same or different and each represents a pyrimidine or purine base or a derivative thereof.

Y is a group represented by the formula (i):

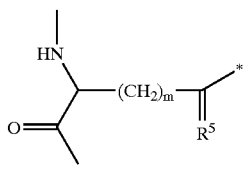
(i)

wherein m is an integer of 1 to 3, $R^5$ represents an oxygen or sulfur atom, and * indicates the site of bonding to A in the nucleoside derivative represented by general formula (1);

represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a single bond, 1 is an integer of 0 to 5, and n is an integer of 2 to 100.

26. The use of the N-protected nucleoside derivative according to claim 21 as a starting material in the production of nucleoside derivatives represented by the general formula:

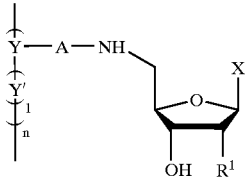

wherein X is(are) the same or different and each represents a pyrimidine or purine base or a derivative thereof, Y and Y' are the same or different and each represents at least one amino acid or amino acid derivative selected from the group consisting of serine, threonine, ornithine, aspartic acid, glutamic acid, lysine, arginine, cysteine, methionine, β-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and β-thiocarbonylhomoglutamic acid, $R^1$ represents a hydrogen atom or a hydroxyl group, A represents a single bond, 1 is an integer of 1 to 5, and n is an integer of 2 to 100.

BEST MODES FOR CARRYING OUT THE INVENTION

Figure 1:
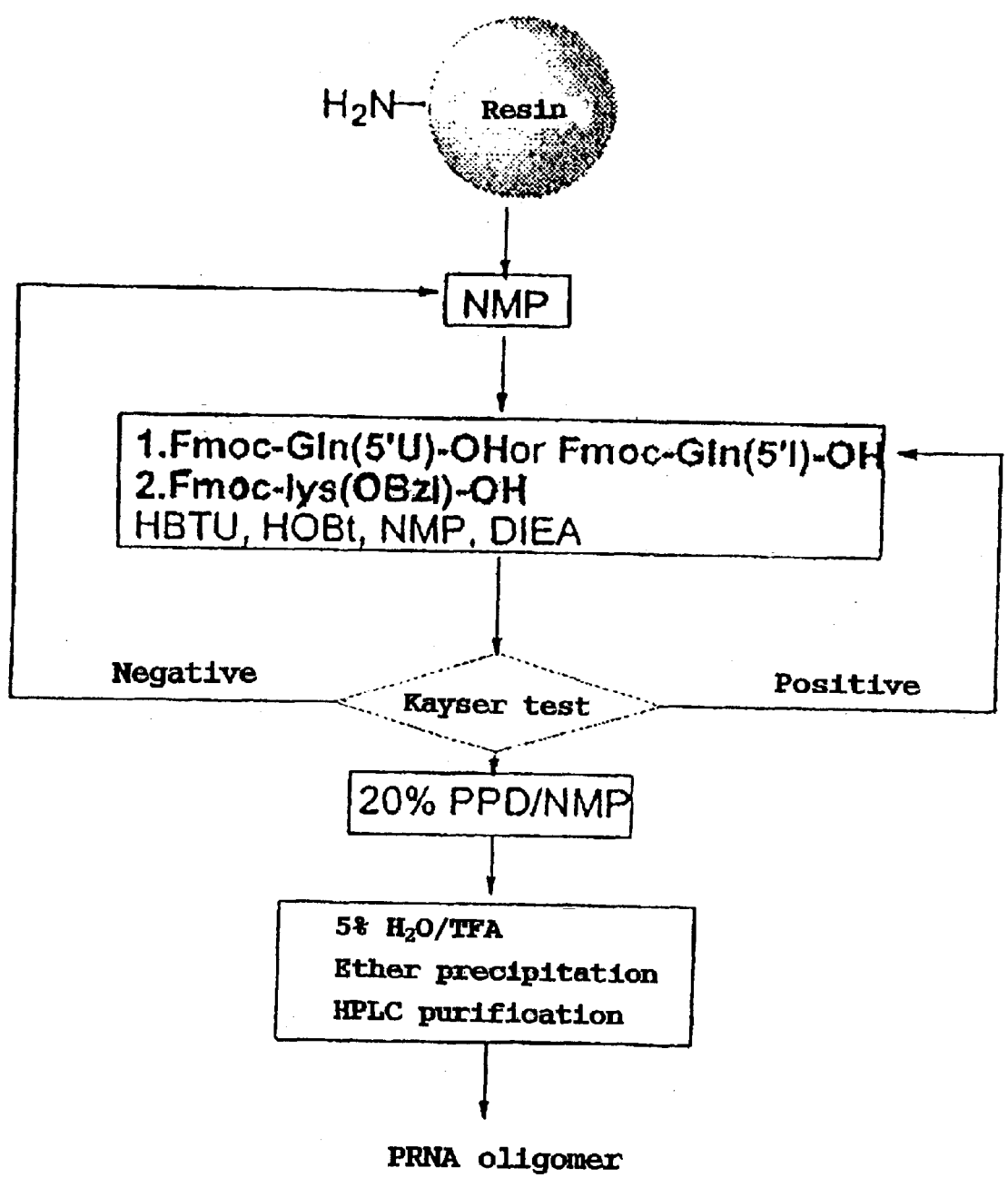
FIG. 1 is a schematic representation of a solid phase process for synthesizing the nucleoside derivatives (PRNA oligomers or polymers) according to the invention.

The nucleoside derivatives of the invention are novel compounds not yet described in the literature and are represented by the following formula (1):

(1)

wherein X is(are) the same or different and each represents a pyrimidine or purine nucleic acid base or a derivative thereof, Y and Y' are the same or different and each represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a single bond or a carbonyl or thiocarbonyl group, 1 is an integer of 0 to 5, and n is an integer of 1 to 100.

The respective groups in the nucleoside derivatives represented by the above general formula (1) are specifically as follows.

The pyrimidine nucleic acid base represented by X includes uracil, cytosine and thymine, while the purine nucleic acid base includes adenine and guanine. The derivatives of these nucleic acid bases are not particular restricted but include, among others, halogenated derivatives, deaminated derivatives, and derivatives having a sulfur atom(s) in lieu of an oxygen atom(s), of uracil, cytosine, thymine, adenine or guanine.

As the uracil derivatives, there may more specifically be mentioned compounds represented by the formula (2):

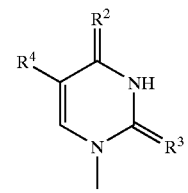
(2)

wherein $R^2$ and $R^3$ are the same or different and each represents an oxygen or sulfur atom, and $R^4$ represents a hydrogen or halogen atom or an alkyl, alkenyl or alkynyl group.

Here, the halogen specifically includes a fluorine atom, a bromine atom, an iodine atom and a chlorine atom. Preferred are a fluorine atom, a bromine atom and an iodine atom.

The alkyl group includes straight or branched lower alkyl groups containing 1 to 6 carbon atoms, such as methyl, ethyl, propyl, isopropyl, butyl, isobutyl, tert-butyl, pentyl and hexyl.

The alkenyl group includes straight or branched lower alkenyl groups containing 1 to 6 carbon atoms, such as vinyl, allyl, propenyl, isopropenyl, 2-methyl-1-propenyl, 2-methylallyl, 3-butenyl, 4-pentenyl, 5-hexenyl, and 1,3-butadienyl.

The alkynyl group includes straight or branched lower alkynyl groups containing 1 to 6 carbon atoms, such as ethynyl, 2-propynyl, 2-butynyl, 2-pentynyl, 2-hexynyl, and 2-penten-4-ynyl.

Thus, more specifically, there may be mentioned halogenated uracil derivatives such as 5-fluorouracil, 5-bromouracil and 5-iodouracil; uracil derivatives having a sulfur atom(s) in lieu of an oxygen atom(s), such as 2-thiouracil, 4-thiouracil and 2,4-dithiouracil; 5-methyluracil, 5-viyluracil, and 5-ethynyluracil; and the like.

As for the cytosine derivatives, there may specifically be mentioned halogenated cytosine derivatives such as 5-fluorocytosine, 5-bromocytosine and 5-iodocytosine; and alkynyl group-containing cytosine derivatives such as 5-ethynylcytosine. Among them, 5-fluorocytosine is preferred.

As the guanine derivatives, there may specifically be mentioned deaminated guanine derivatives such as hypoxanthine, and halogenated guanine derivatives such as 8-fluoroguanine, 8-bromoguanine and 8-iodoguanine. Preferred are hypoxanthine and 8-bromoguanine.

As the adenine derivatives, there may specifically be mentioned 1,$N^6$-ethenoadenine representable by the formula:

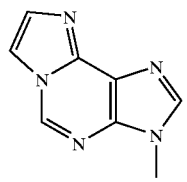

as well as halogenated adenine derivatives such as 8-fluoroadenine, 8-bromoadenine and 8-iodoadenine. Preferred are 1,$N^6$-ethenoadenine and 8-bromoadenine.

The nucleoside derivatives (1) of the invention may have one of the above-mentioned bases or two or more different base species as the base (X) of nucleic acid in each molecule. As preferred nucleic acid base species, there may be mentioned uracil, thymine, cytosine, guanine and adenine.

In the general formula (1), the amino acid or amino acid derivative represented by Y or Y' is not particularly restricted provided that it does not manifest immunogenicity upon polymerization thereof (oligoamino acid, polyamino acid). Specifically, it includes serine, threonine, aspartic acid, glutamic acid, lysine, arginine, cysteine, methionine, ornithine and like amino acids; as well as δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, ω-thiocarbonylamino acids (β-thiocarbonylaspartic acid, γ-thiocarbonylglumatic acid, δ-thiocarbonylhomoglumatic acid, etc.), and like amino acid derivatives. Preferred are glutamic acid, aspartic acid, homoglutamic acid, β-thiocarbonylaspartic acid, γ-thiocarbonylglutamic acid, δ-thiocarbonylhomoglutamic, and N-aminoethylglycine. These amino acids and amino acid derivatives may be in the d-form, l-form or racemic form.

The N-terminal of the amino acid or amino acid derivative represented by —(T-(Y')$_1$)$_n$—, either in the monomer or polymer form, may be a free amino acid or have an arbitrary functional group having an amide, carbamic acid, thiocarbamic acid, urea, thiourea or phosphoramide bond, for instance, without any particular restriction. The C terminal may also be a free carboxyl group or have an arbitrary functional group having an amide or ester bond, for instance, without any particular restriction.

The amino acid or amino acid derivative represented by Y is bound to the 5'-carbon of the sugar-base moiety through amide, thioamide, carbamic acid, thiocarbamic acid, dithiocarbamic acid, urea, thiourea, ester or like bonding. The position in the amino acid or amino acid derivative which is bound to said 5'-carbon is not particularly restricted. For example, an amide bond may be formed between the 5'-amino group of the sugar-base moiety and the α- or β-carboxyl group of aspartic acid, which is a dicarboxylic acid, the α- or γ-carboxyl group of glutamic acid, or the α- or δ-carboxyl group of homoglutamic acid, and a thioamide bond may be formed between the 5'-amino group of the sugat-base moiety and the α-thiocarboxyl group of β-thiocarbonylaspartic acid or the γ-thiocarboxyl group of γ-thiocarbonylglutamic acid. In the case of lysine, which is a diamine, the above-mentioned bond may be formed between the α-amino group or ε-amino group and the 5'-amino group and, in the case of serine, between the β-hydroxyl group and the 5'-amino group.

In accordance with the present invention, 1 is generally an integer of 0 to 5, preferably an integer of 0 to 2, more preferably an integer of 0 or 1.

In accordance with the present invention, n is generally an integer of 1 to 100, preferably an integer of 6 to 50, more preferably an integer of 8 to 20.

The nucleoside derivate according to the present invention includes the so-called "amino acids-nucleoside", in the monomer form (l=0, n=1) and polymer form (l=0, n=2 to 100), in which the 5'-amino group of a 5'-amino-nicleoside is bound, either directly or via a carbonyl or thiocarbonyl group or a carbamic acid, thiocarbamic acid, urea or thiourea bond, to the above-mentioned amino acid or amino acid derivative (herein, also referred to as "amino acids"), as well as the so-called "oligo- or polyamino acids-nucleoside", in the monomer form (l=1 to 5, n=1) or polymer form (l=1 to 5, n=2 to 100), in which the 5' amino group of a 5'-amino-nucleoside is bound, either directly or via a carbonyl or thiocarbonyl group or a carbamic acid, thiocarbamic acid, urea or thiourea bond, to a polymer of one of the above "amino acids" (oligoamino acids, polyamino acids).

The nucleoside derivatives of the invention include more specifically the compounds I, II and III shown below.

Compounds I:

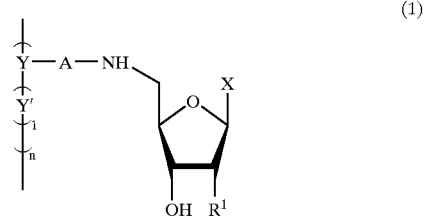

(1)

wherein X, Y', $R^1$, l and n are as defined above, and A represents a single bond; or Y is represented by the following formula (i):

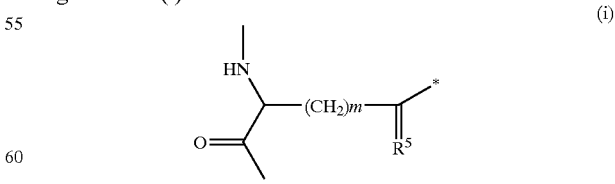

(i)

wherein m is an integer of 1 to 3, $R^5$ represents an oxygen or sulfur atom, and * indicates the site of binding to A in the nucleoside derivative represented by the general formula (1).

Compounds II:

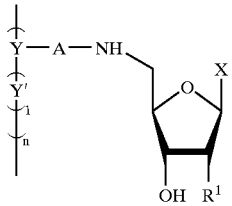

wherein X, Y', $R^1$, l and n are as defined above, and A represents a single bond; or Y is represented by the following formula (ii);

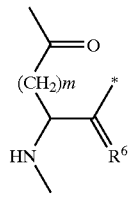

wherein m is an integer of 1 to 3, $R^6$ represents an oxygen or sulfur atom, and * indicates the site of binding to A in the nucleoside derivative represented by the general formula (1).

Compounds III:

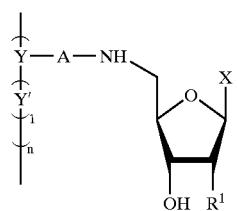

wherein X, Y', $R^1$, l and n are as defined above, and A represents a carbonyl or thiocarbonyl group: or Y is represented by the following formula (iii):

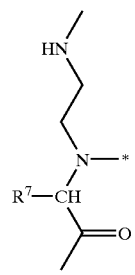

wherein $R^7$ represents a hydrogen atom or a carboxymethyl, carboxyethyl, hydroxymethyl, aminobutyl, aminopropyl or 4-amino-3-hydroxypropyl group, and * indicates the site of binding to A in the nucleoside derivative represented by the general formula (1).

The nucleoside derivatives represented by the above formulas I, II and III are hereinafter referred to as PRNA1 (α type), PRNA2 (γ type) and PRNA3 (AEG type), respectively.

The nucleoside derivatives of the invention can be produced by various methods. In the case of PRNA1, for instance, those nucleoside derivatives (1-i) (where l=0) which have a group represented by the formula (i) as the group Y can be produced in the following manner.

Reaction formula 1

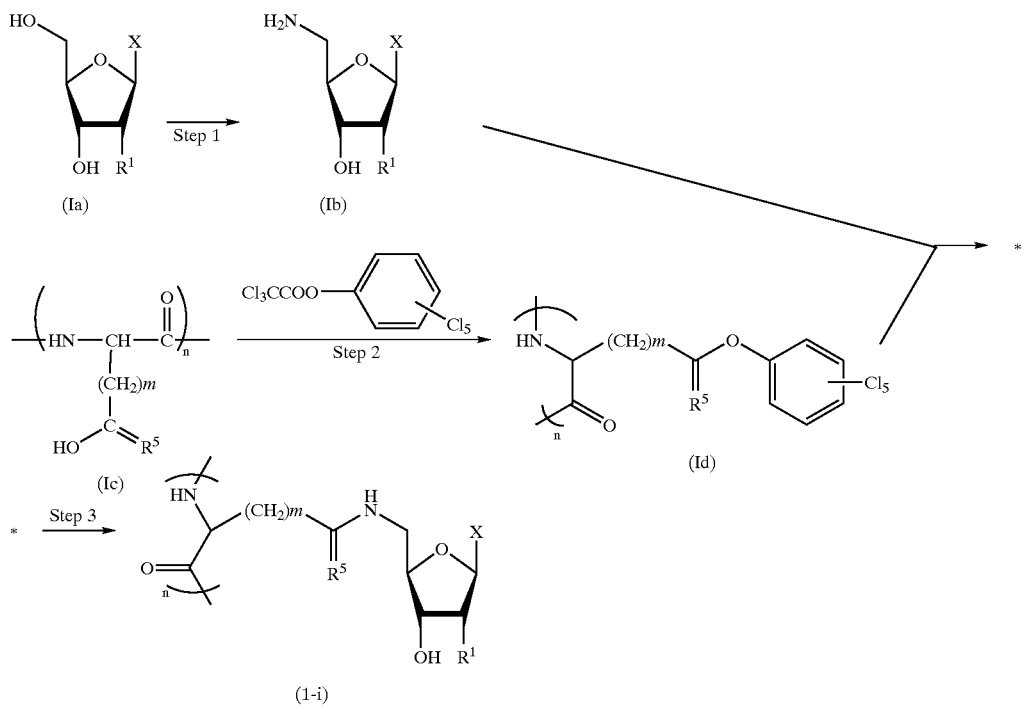

(In the formula, X, $R^1$, $R^5$, m and n are as defined above.)

In accordance with the reaction formula 1, a 5'-amino-nucleoside derivative (1b) is produced by aminating the hydroxyl group (5'-hydroxyl group) bound to the 5' carbon in the sugar moiety of a nucleoside or nucleoside derivative of the general formula (1a) (step 1). Separately, an amino acid derivative (1d) is produced by reacting such an amino acid (1c) as L-aspartic acid, D-aspartic acid, β-thiocarbonyl-L-aspartic acid, β-thiocarbonyl-D-aspartic acid (in all the above, m=1), L-glutamic acid, D-glutamic acid, γ-thiocarbonyl-L-glutamic acid, γ-thiocarbonyl-D-glutamic acid (in the above, m=2), L-homoglutamic acid, D-homoglutamic acid, δ-thiocarbonyl-L-homoglutamic acid or δ-thiocarbonyl-D-homoglutamic acid (in the above, m=3) with pentachlorophenyl trichloroacetate (step 2). The nucleoside derivative (1b) and amino acid derivative (1d) respectively produced in the above steps are reacted with each other, whereby the nucleoside derivative (1-i) of the invention can be produced (step 3).

In step 1, various methods of substituting an amino group for a hydroxyl group can be used. Specifically, the method of Mitsunobu (T. Hata, et al., J. Chem. Soc., Perkin 1, 306 (1976); T. Hata, et al., Chem. Lett., (1975), pp. 977–980), for instance, can be applied. Specifically, the step can be carried out according to the following formula.

<Step 1>

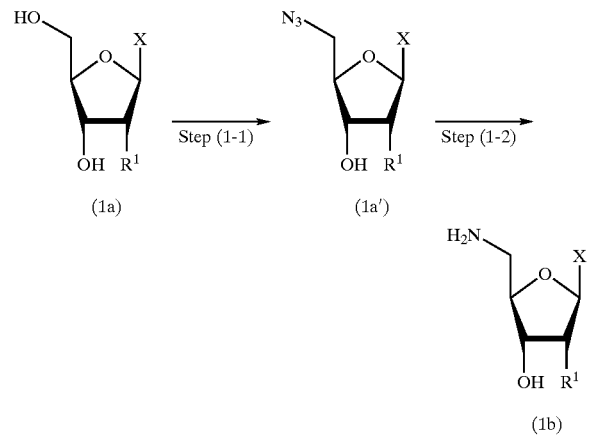

(In the formula, X and $R^1$ are as defined above.)

The step (1-1) involves a reaction for converting the 5'-hydroxyl group of the nucleoside or nucleoside derivative (1a) to an azido group. When the nucleoside or nucleoside derivative (1a) is reacted with triphenylphosphine ($PPh_3$), lithium azide ($LiN_3$) and carbon tetrabromide ($CBr_4$) in an appropriate solvent, for instance, the 5'-$N_3$-nucleoside derivative (1a') can be obtained.

Here, the reaction solvent includes hydrocarbon solvents such as cyclohexane, benzene and toluene; halogenated hydrocarbon solvents such as dichloromethane, chloroform, dichloroethane, trichloroethane and chlorobenzene; water; alcohol solvents such as methanol, ethanol and isopropanol; carboxylic acids such as formic acid and acetic acid; ether solvents such as tetrahydrofuran and dioxane; acetic anhydride; acetone; dimethylformamide, dimethyl sulfoxide; acetonitrile; THF; methylene chloride, etc. Preferred are dimethylformamide and dimethyl sulfoxide, and they are used preferably after drying. The amount of the solvent is generally 20 to 1000 parts by weight, preferably about 50 to 100 parts by weight, per part by weight of the nucleoside or nucleoside derivative of general formula (1a).

Triphenylphosphine, lithium azide and carbon tetrabromide are used each preferably in an amount of about 1 to 10 moles per mole of the nucleoside or nucleoside derivative of general formula (1a).

Such reaction can be carried out generally within the range of 0 to 80° C., and will be complete in about 1 to 36 hours. The reaction is terminated by addition of a polar solvent such as methanol, and the solvent is then distilled off. The 5'-$N_3$-nucleoside derivative (1a') can be isolated by further carrying out an ordinary purification procedure such as column chromatography, as necessary.

The step (1-2) involves a reaction for converting the azido group of the above 5'-$N_3$-nucleoside derivative (1a') to an amino group and can be carried out, for example, by reacting with hydrogen in an appropriate solvent. This reaction is preferably carried out in the presence of such a catalyst as palladium-on-carbon or ruthenium-on-carbon.

Here, the reaction solvent includes hydrocarbon solvents such as cyclohexane, benzene and toluene; halogenated hydrocarbon solvents such as dichloromethane, chloroform, dichloroethane, trichloroethane and chlorobenzene; water; alcohol solvents such as methanol, ethanol and isopropanol; carboxylic acids such as formic acid and acetic acid; ether solvents such as tetrahydrofuran and dioxane; acetic anhydride; acetone, dimethylformamide, dimethyl sulfoxide and like polar solvents, among others. Preferred are alcohols such as methanol and ethanol and dimethylformamide. The amount of the solvent is generally 20 to 1000 parts by weight, preferably about 50 to 100 parts by weight; per part by weight of the 5'-$N_3$-nucleoside or 5'-$N_3$-nucleoside derivative of general formula (1a').

Such reaction can be carried out generally at room temperature, preferably within the range of 0 to 50° C., and will be complete in about 0.5 to 48 hours. After completion of the reaction, the reaction mixture filtrate is concentrated, and the residue is reprecipitated using a methanol-based solvent, for instance, whereby the 5'-$NH_2$-nucleoside derivative (1b) can be obtained. Desirably, a mixed solvent composed of methanol and ethanol is used as the methanol-based solvent.

<Step 2>

The step 2 can be carried out by reacting the amino acid (1c) with pentachlorophenyl trichloroacetate in an appropriate solvent.

Here, the reaction solvent include hydrocarbon solvents such as cyclohexane, benzene and toluene; halogenated hydrocarbon solvents such as dichloromethane, chloroform, dichloroethane, trichloroethane and chlorobenzene; water; alcohol solvents such as methanol, ethanol and isopropanol; carboxylic acids such as formic acid and acetic acid; ether solvents such as tetrahydrofuran and dioxane; acetic anhydride; acetone; dimethylformamide; acetonitrile; THF; methylene chloride, etc. Preferred are dimethylformamide, dimethyl sulfoxide and like polar solvents. The amount of the solvent is generally 10 to 1000 parts by weight, preferably about 20 to 100 parts by weight, per part by weight of the amino acid. Said reaction can be carried out within the range of 0 to 80° C. and will be complete in about 0.5 to 48 hours.

<Step 3>

The step 3 can be carried out by adding the 5'-$NH_2$-nucleoside derivative (1b) obtained in the above step 1 to the reaction mixture of the above step 2, followed by mixing, whereby the nucleoside derivative (PRNA1) of the invention as represented by the general formula (1-i) can be obtained. The proportions of the 5'-$NH_2$-nucleoside derivative (1b) and amino acid derivative. (1d) to be subjected to the reaction are not particularly restricted but mention may be made of the range of about 0.8 to 1 mole of the polyamino acid derivative (1d) per mole of the 5'-$NH_2$-nucleoside derivative (1b). The reaction is carried out within the range of 0 to 40° C., preferably 0 to 40° C., and will be complete generally in about 24 to 48 hours.

The reaction product obtained by each of the above-mentioned reactions can be isolated from the reaction system and further purified by the conventional means known in the art. Such method of purification includes recrystallization, column chromatography, preparative thin layer chromatography, solvent extraction and reprecipitation, among others.

In the case of PRNA2, for instance, those nucleoside derivatives (where l=0) which have a group represented by the formula (ii) as the Y group can be produced by the process shown below in terms of reaction formula 2.

(1b), via the 5'-amino group thereof, to the α-carboxyl group of an amino acid whose amino and carboxyl groups are both protected (step 1), and the nucleoside derivative of the invention is then produced by using the monomer obtained as an unit and subjecting the same to consecutive elongation at the N terminus and C terminus thereof by repeating a selective deprotection and condensation cycle (steps 2 to 4). The amino acid mentioned above includes those having two carboxyl groups per molecule, such as L-aspartic acid, D-aspartic acid, β-thiocarbonyl-L-aspartic acid, Reaction formula 2

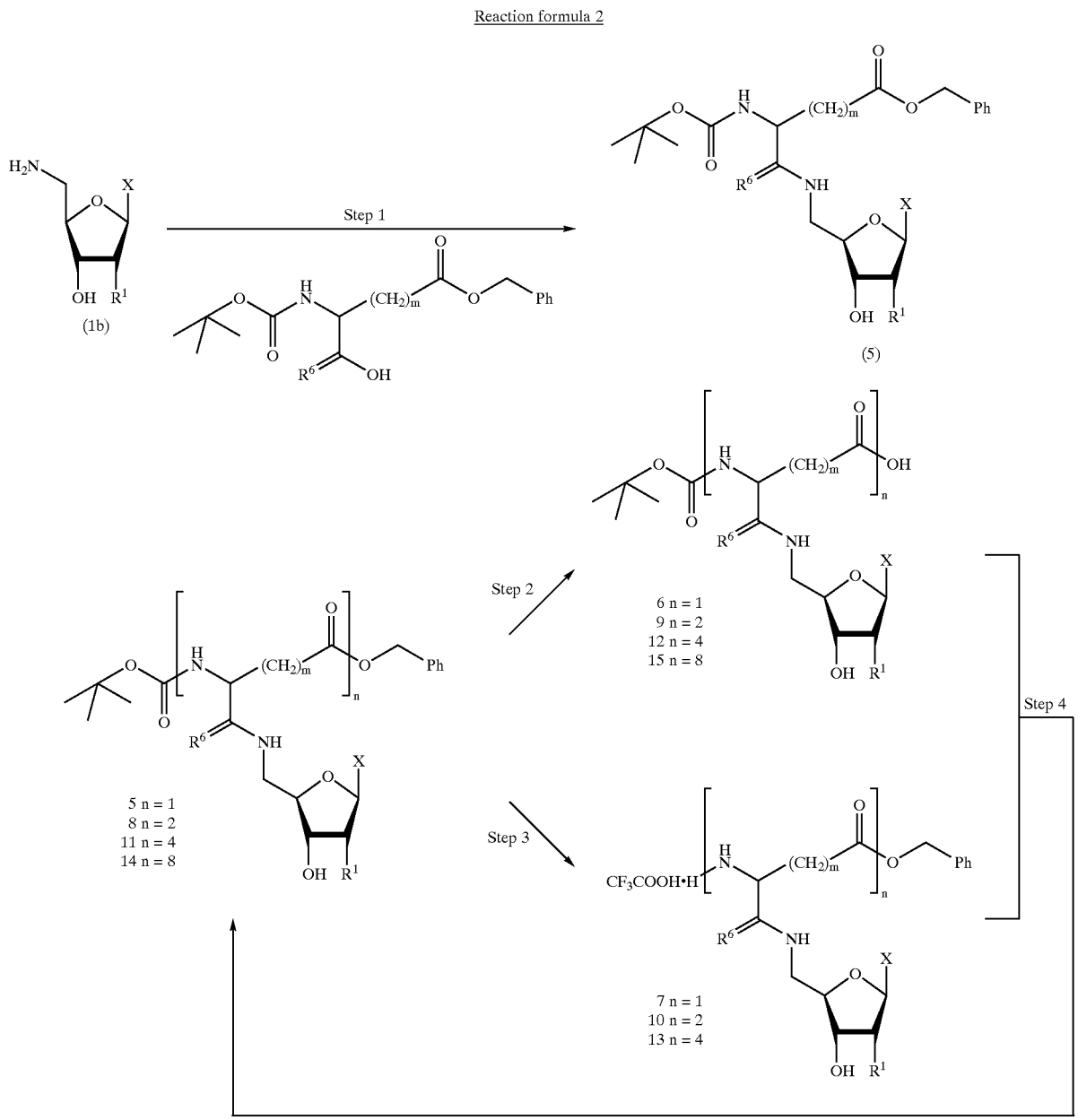

(In the formula, X, $R^1$, $R^6$ and m are as defined above.)

According to the reaction formula 2, a monomer (compound 5) composed of an amino acid serving as the peptide main chain and a nucleoside bound thereto is synthesized by coupling the 5'-$NH_2$-nucleoside derivative β-thiocarbonyl-D-aspartic acid (in all the above, m=1), L-glutamic acid, D-glutamic acid, γ-thiocarbonyl-L-glutamic acid, γ-thiocarbonyl-D-glutamic acid (in the above, m=2), L-homoglumatic acid, D-homoglutamic acid, δ-thiocarbonyl-L-homoglutamic acid and δ-thiocarbonyl-D-homoglutamic acid (in the above, m=3).

<Step 1>

As mentioned above, the step 1 involves a reaction for coupling the α-carboxyl group of the amino acid or amino acid derivative serving as the peptide main chain unit to the 5'-amino group of the nucleoside derivative, and uses, as the starting materials, the amino acid derivative whose amino group and whose carboxyl group (e.g. ω-carboxyl group) other than the one at the α position are protected, and the 5'-NH$_2$-nucleoside derivative (1b) produced in the above mentioned <step 1>, namely according to the process of reaction formula 1.

The amino-protecting group for the amino acid, which is to be used here, includes a wide variety of amino-protecting groups commonly used in peptide synthesis. As such amino-protecting groups, there may be mentioned, for example, carbobenzoxy, tert-butylbxycarbonyl, 9-fluorenylmethoxycarbonyl, phthalyl, formyl, acetyl, trifluoroacetyl, p-toluenesulfonyl, triphenylmethyl, cyclohexyloxycarbonyl, o-nitrophenylsulfenyl, tert-amyloxycarbonyl, benzyl, alkyl- or allylthiocarbonyl, o-nitrophenoxyacetyl, chloroacetyl, benzenesulfonyl, dibenzylphosphoryl, trialkylsilyl, allylidene, and acetoacetyl, which may optionally be substituted. Preferred from the high yield and highly selective deprotection viewpoint are tert-butyloxycarbonyl and 9-fluorenylmethoxycarbonyl. The former, which is an amino-protecting group allowing deprotection under acidic conditions, is useful especially in the liquid phase synthesis of the nucleoside derivatives of the invention, while the latter, which is an amino-protecting group allowing deprotection under basic conditions, is useful especially in the solid phase synthesis of the nucleoside derivatives of the invention.

As the carboxyl-protecting group for the amino acid, there may generally be mentioned esters such as methyl ester, ethyl ester, tert-butyl ester, benzyl ester and p-nitrobenzyl ester, as well as N'-substituted hydrazides; among others. Preferred from the high yield and highly selective deprotection viewpoint are the benzyl ester and p-nitrobenzyl ester, which can be eliminated by catalytic hydrogenation.

As more preferred specific examples of the amino acid or amino acid derivative, there may be mentioned amino acids or amino acid derivatives whose amino group is protected by a tert-butyloxycarbonyl group (Boc-) and whose carboxyl group is either free or protected by a benzyl ester group (-OBzl), and amino acids and amino acid derivatives whose amino group is protected by a 9-fluorenylmethoxycarbonyl group (Fmoc-) and whose carboxyl group is either free or protected by a benzyl ester group (-OBzl). The above-mentioned N,γC-protected amino acids resulting from introduction of an arbitrary protective group(s) thereinto can all be produced by a conventional method.

The above coupling reaction between the N,γC-protected amino acid and 5'-NH$_2$-nucleoside derivative (1b) can be carried out in the manner of amide bond formation reaction using a condensing agent, such as DCC (dicyclohexylcarbodiimide), WSC (water-soluble dicyclohexylcarbodiimide-) or BOP (benzotriazole-1-yloxytris(dimethylamino)phosphonium hexafluorophosphate), and an additive agent, such as HOBt (1-hydroxybenzotriazole), HONSu (N-hydroxysuccinimide), paranitrophenol, pentafluorophenol or pentachlorophenol. Such reaction can be carried out in DMF (N,N-dimethylformamide), DMSO (dimethyl sulfoxide), CHCl$_3$, CH$_2$Cl$_2$, CH$_3$CN or some other nonpolar solvent in the presence of diisopropylethylamine, and such reaction leads to formation of the monomer (compound 5).

The monomer (5) formed can be isolated and purified from the reaction mixture by a conventional method. More specifically, there may be mentioned the method comprising removing the solvent from the reaction mixture, extracting the product from the residue using ethyl acetate and, then, purifying the same utilizing the technique of column chromatography, for instance.

<Steps 2 to 4>

In the steps 2 to 4, an oligomer is formed by subjecting the monomer (5) obtained in the above <step 1>, as a unit, to condensation/elongation reaction. More specifically, in those steps, the oligomer (polymer) is produced by repetition of a reaction cycle (selective deprotection-condensation/repetition cycle) comprising the selective deprotection reactions of the carboxyl terminus and amino terminus of the above monomer (steps 2 and 3) and the subsequent condensation reaction (step 4) (selective deprotection-condensation cycle).

More detailedly, the selective deprotection-condensation cycle is carried out in the following manner.

① First, the benzyl ester group, namely the carboxyl-protecting group, of the N,C-protected monomer (5) formed in the above <step 1> is eliminated by catalytic hydrogenation to give the corresponding free carboxyl group-containing N-protected monomer (compound 6, n=1) (step 2).

② Separately, the tert-butyloxycarbonyl group, namely the amino-protecting group, of the N,C-protected monomer (5) formed in the above <step 1> is eliminated by acid treatment using trifluoroacetic acid, for instance, to give the corresponding free amino group-containing C-protected monomer (compound 7, n=1) (step 3).

③ Thereafter, the compound 6 and compound 7 respectively formed by the reactions in the above step 2 and step 3 are subjected to condensation by an amide bond formation reaction using the reagents HOBt and BOP, whereby the dimer (compound 8, n=2) is formed (step 4).

When the above cycle comprising the steps ① to ③ is repeated, the PRNA oligomer whose carboxyl and amino groups are protected can be produced (two repetitions: tetramer (compound 11); three repetitions: octamer (compound 14)).

The preparation of the PRNA2 (γPRNA) having a free amino group and a free carboxyl group can be carried out in the conventional manner by eliminating the amino-protecting group and carboxyl-protecting group from the N-,C-protected PRNA oligomer obtained as mentioned above. The process described in Example 3 may be mentioned as a specific example.

As mentioned above, the nucleoside derivative (1) of the present invention in which A, in general formula (1), is a single bond can be produced according to the process represented by the reaction formula 1 or 2.

In the case of PRNA3, for instance, those nucleoside derivatives (1-iii) (where l=0) having a group represented by the formula (iii) as the Y group can be produced according to the process represented by the following reaction formula 3.

Reaction formula 3

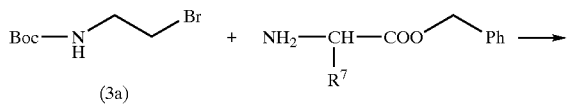

(3a)

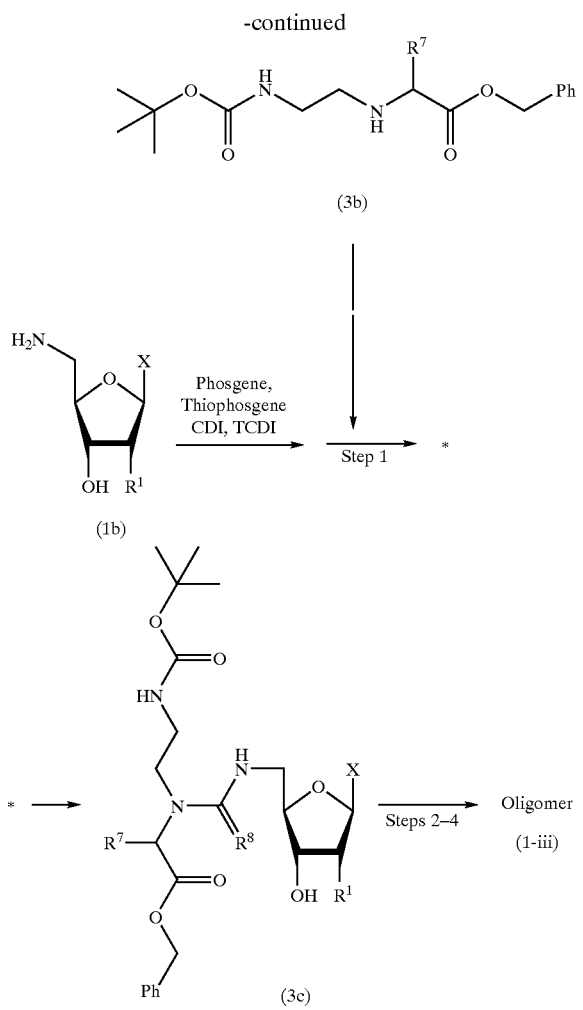

(In the formula, X, $R^1$ and $R^7$ are as defined above and $R^8$ represents an oxygen or sulfur atom.)

According to the reaction formula 3, a monomer (compound 3c) composed of a peptide main chain and a nucleoside bound thereto is synthesized by coupling the 5'-$NH_2$-nucleoside derivative (compound 1b), via the 5'-amino group thereof, to the α-amino group of an amino acid (compound 3b) whose amino and carboxyl groups are both protected (step 1), and the monomer (3c) obtained is then used as a unit and subjected to elongation using an amide bond formation reaction to give a nucleoside derivative (1-iii) of the invention (steps 2 to 4).

As for the amino-protecting group and carboxyl-protecting group, those protective groups mentioned hereinbefore referring to PRNA2s can all be used. In cases where aminoethyleneglycine (AEG) ($R^7$ being a hydrogen atom) is used as the peptide main chain, Boc-AEG-OBn produced by using ethylenediamine as a starting material is judiciously used as the compound having protective groups at the N terminus and C terminus.

More specifically, the steps are performed in the following manner.

A Boc group can be introduced into 2-bromoethylamine (3a) by a conventional method, specifically by adding di-tert-butyl dicarbonate (($Boc)_2O$) dropwise to a solution of 2-bromoethylamine (3a) in an appropriate solvent. Here, dioxane, THF, dimethylformamide, chloroform, methylene chloride or the like may be used as the solvent. Di-tert-butyl dicarbonate is used generally in amount of 1 to 2 moles, preferably about 1.2 moles, per mole of 2-bromoethylamine (3a). Preferably, the dropping is conducted within the range of −10 to 20° C.

The reaction product (N-protected compound) is then isolated and purified from the reaction mixture by a conventional method. More specifically, water is added to the residue after removal of the solvent from the reaction mixture, and the resulting aqueous layer is extracted with a nonpolar organic solvent such as chloroform. Then, the N-Boc-protected compound that has migrated to the organic layer is purified by utilizing column chromatography, for instance.

Then, an amino acid in the form of a benzyl ester derivative is reacted with the N-protected compound obtained as described above, whereby a butoxycarbonyl group is introduced into the amino group of the amino acid benzyl ester derivative (Boc-amino acid derivative-OBn, N,C-protected amino acid derivative) (3b). Such reaction can be carried out in a solvent such as chloroform, methylene chloride, dioxane, dimethylformamide or dimethyl sulfoxide. The amounts of diisopropylethylamine and benzyl bromoacetate are about 0.5 to 2 moles and about 1 to 2 moles, respectively, per mole of N-Boc-1,2-aminoethane. The reaction is preferably carried out within the range of 0 to 60° C. Generally, such reaction will be complete in 0.5 to 24 hours.

The reaction product (N,C-protected amino acid derivative) (3b) produced by the above reaction can be isolated from the reaction system and purified in conventional means known in the art. As such a method of purification, there may be mentioned recrystallization, column chromatography, preparative thin layer chromatography, and solvent extraction, among others.

In Step 1, the 5'-$NH_2$-nucleoside derivative (1b) synthesized by the process of reaction formula 1 (step 1) is then reacted with the N,C-protected amino acid derivative (3b) obtained as described above, whereby the N,C-protected PRNA3 monomer (3c) can be produced. In this case, it is preferred that the 5'-$NH_2$-nucleoside derivative (1b) be reacted in advance with N,N'-carbonyldiimidazole (CDI), phosgene, N,N'-thiocarbonyldiimidazole (TCDI) or thiophosgene and the thus-obtained reaction product be reacted with the above N,C-protected amino acid derivative (3b). Such reactions can be carried out in DMF, chloroform, methylene chloride, dimethyl sulfoxide or some other nonpolar solvent.

The proportion of the above-mentioned CDI or the like per mole the 5'-$NH_2$-nucleoside derivative (1b) is generally about 1 to 2 moles, preferably about 1 mole. Such reaction is preferably carried out at a low temperature, generally within the range of −120 to 0° C., preferably −78 to −40° C., so that side reactions involving the 3' and/or 2' hydroxyl group of the 5'-$NH_2$-nucleoside derivative (1b) may be inhibited. After 0.5 to 2 hours of reaction, the reaction system is returned to room temperature, and the N,C-protected amino acid derivative (3b) is added. The proportion of the N,C-protected amino acid derivative (3b) is generally about 1 to 2 moles, preferably about 1 to 1.5 moles, per mole of the 5'-$NH_2$-nucleoside derivative (1b).

The reaction product (N,C-protected PRNA3 monomer (3c)) produced by the above reaction is isolated from the reaction system and purified by conventional means known in the art. As such method of purification, there may be mentioned recrystallization, column chromatography, preparative thin layer chromatography, solvent extraction and reprecipitation. The isolation and purification of the above product is preferably carried out at room temperature or a lower temperature.

Then, the thus-obtained N,C-protected PRNA3 monomer (3c) can be oligomerized by a conventional method, for example by repeating the so-called selective deprotection-condensation cycle comprising the carboxyl-protecting group elimination step 2, the amino-protecting group elimination step 3 and the step 4 in which the C-deprotection production and N-deprotection product are condensed under amide bond formation, as mentioned hereinabove referring to PRNA2s, or by the solid synthesis method, sequential condensation method, and fragment condensation method.

Those nucleoside derivatives in which A in general formula (1) is a carbonyl group can be produced by using, as a starting material, serine, threonine, aspartic acid, glutamic acid, lysine, arginine, cysteine or ornithine, δ-hydroxylysine, N-aminoethylglycine, N-aminoethylserine, N-aminoethyllysine, N-aminoethylornithine, N-aminoethylaspartic acid, N-aminoethylglutamic acid, or a oligomer or polymer thereof and reacting the same with N,N'-carbonyldiimidazole (CDI), phosgene or the like. Those nucleoside derivatives in which A is thiocarbonyl can be produced by using the above amino acid derivative or an oligomer or polymer thereof as-a starting material and reacting the same with N,N'-thiocarbonyldiimidazole, thiophosgene or the like.

The nucleoside derivative of the invention includes those mononucleoside derivatives (PRNA monomers) represented by the general formula (1) in which the amino group of the amino acid or amino acid derivative represented by —(Y—(Y')$_1$)$_n$— (1 being an integer of 0 to 5 and n being 1) or the amino group at the N terminus thereof is protected by a tert-butoxycarbonyl (Boc) or 9-fluorenylcarbonyl (Fmoc) group and the carboxyl group at the C terminus is either free or protected by a benzyl ester group. The 9-fluorenylcarbonyl (Fmoc) group is an amino-protecting group capable of being eliminated reversibly under basic conditions. Therefore, the mononucleoside derivatives whose N-terminus is protected by a Fmoc group are useful as Fmoc-PRNA monomers (Fmoc-mononucleoside derivatives), which are starting materials for the solid synthesis of oligo- or polynucleoside derivatives.

The Fmoc-mononucleoside derivatives (Fmoc-PRNA monomers) can be prepared as mononucleoside derivatives whose C terminal carboxyl group is protected by a benzyl ester group by using, as a starting material, the compound 5 (N,C-protected PRNA2 monomer) prepared in accordance with the reaction formula 2 given hereinabove or the compound 3c (N,C-protected PRNA3 monomer) prepared in accordance with the reaction formula 3, and first eliminating (deprotecting) the N terminal Boc group with TFA and then introducing an Fmoc group using Fmoc-Osu (N-(9-fluorenylcarbonyloxy)succinimide). Those mononucleoside derivatives (PRNA monomers) 9 having a free carboxyl group can be prepared by eliminating the C-terminal protective group by a conventional method, for example by catalytic reduction. The solvent to be used in catalytic reduction, in particular DMF, is preferably used after purification so that it be free of a free amine.

By providing the above-mentioned Fmoc-mononucleoside derivatives, in particular Fmoc-PRNA monomers, the present invention can provide a process for solid phase synthesis of oligo- or polynucleoside derivatives using such derivatives as starting materials. Such solid phase synthesis makes it possible to automatically synthesize the oligo- or polynucleoside derivatives of the invention using an apparatus.

The solid phase synthesis of the oligo- or polynucleoside derivative of the invention can be achieved by using the above-mentioned Fmoc-mononucleoside derivative (Fmoc-PRNA monomer) as a monomeric starting material and repeating the coupling and elimination reactions according to those solid phase method of synthesizing peptides which are known in the art (e.g. G. R. Marchall, R. B. Merrifield, "Biochemical Aspects of Reactions on Solid Supports", Ed. by G. R. Stark, p. 111–169, Academic Press, N.Y. (1971) etc.). The solid phase to be used in the above synthesis can be selected from a wide variety of solid carriers or supports that have been used in the art in solid phase synthesis of peptides. The coupling reaction is preferably carried out while checking the introduction of the Fmoc-mononucleoside derivatives (Fmoc-PRNA monomers) one by one by the Kayser test using ninhydrin. By doing so, the oligo- or polynucleoside derivatives can be produced in high yields. A specific process for solid phase synthesis of the oligo- or polynucleoside derivatives of the invention will be described later herein in the example section. Basically, however, they can be produced via the step of introducing an Fmoc-mononucleoside derivative (Fmoc-PRNA monomer) onto a solid phase carrier (step 1), the step of eliminating the amino-protecting group of the Fmoc-nucleoside derivative (Fmoc-PRNA) (step 2), the step of subjecting an Fmoc-mononucleoside derivative (Fmoc-PRNA monomer) to condensation with the N-deprotected nucleoside derivative at the N terminus thereof (step 3), the step of successive extension using mononucleoside derivatives (PRNA monomers) by repeating the coupling reaction of step 3 and the elimination reaction of step 2 (step 4), and the step of excising the nucleoside derivative polymer obtained from the solid phase carrier (step 5). It is also possible to carry out a condensation reaction confirmation test, such as the Kayser test, for confirming the extent of progress of the condensation reaction after step 3. The Fmoc-PRNA monomer condensation for elongation can be securely realized by carrying out such reaction confirmation test after each condensation reaction.

The nucleoside derivative (1) of the invention can be used as an antisense molecule in the antisense method. In this case, the nucleoside derivative of the invention can be used either as such or in the form incorporated as a part of the nucleotide sequence of a DNA or RNA sequence or a DNA/RNA derivative, namely in the form of the so-called chimera molecule. Here, the DNA or RNA derivative includes not only those equivalent in physiological function to nucleic acids such as DNAs and RNAs but also nucleic acid derivatives known in the art as antisense molecules such as PNAs and other nucleic acid analogues that are currently known or will be found in the future. As examples of the DNA or RNA derivatives, for instance, there may be mentioned those represented by the following formula:

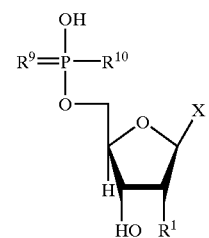

(In the formula, X and $R^1$ are as defined above, $R^9$ represents an oxygen or sulfur atom, $R^{10}$ represents $O^-$, $S^-$, $NH_2$, $NHR^{11}$, $NR^{11}R^{12}$, or $R^{11}$. $R^{11}$ and $R^{12}$ are the same or different and each represents $CH_3$, $(CH_2)_nCH_3$, $(CH_2)_nNHZ$, $(CH_2)_nNZZ'$, or $(CH_2)_nNH_2$ [in which Z and Z' are the same or different and each represents a lower alkyl group containing 1 to 4 carbon atoms, such as methyl, ethyl, isopropyl, n-propyl, tert-butyl, isobutyl or n-butyl, and n is an integer of 0 to 10].)

The nucleoside derivative of the invention can be coupled to a DNA or RNA, or a derivative thereof, either directly or via a spacer. The mode of such bonding is not particularly restricted but includes, in the case of direct bonding, the modes of bonding of the 3' or 5' terminus of the nucleoside derivative to the 5' or 3' terminus of a DNA or a derivative thereof via a phosphodiester, methylphosphonate, methylphosphonothioate, phosphorothioate, amide, sulfomaide, ethylene glycol, or thioformal bond, among others. As the mode of bonding of the nucleoside derivative of the invention to a DNA or RNA or a derivative thereof via a spacer, there may be mentioned, for example, those resulting from coupling of the 5'-amino group of a DNA or RNA or a derivative thereof to the carboxyl group of the nucleoside derivative via a lower alkylene group containing 1 to 10 carbon atoms $((CH_2)_n$, n=1 to 10), such as a methylene, ethylene, propylene or butylene group, or a polymer of a lower alkyleneoxy group containing 1 to 4 carbon atoms, such as a methyleneoxy or ethyleneoxy group, for example $(CH_2O)_n$ or $(CH_2CH_2O)_n$ (n=1 to 10).

Such coupling of the nucleoside derivative to a DNA or RNA or a derivative thereof can be carried out by a conventional method.

The nucleoside derivative of the invention and the above chimera molecule containing said derivative can be prepared in the form of pharmaceutical preparations by compounding the same with conventional, pharmacologically acceptable additives, such as buffers, stabilizers and diluents, and a carrier therefor. Such preparations can be applied to mammals, including humans, and various dosage forms can be employed according to the intended purpose of administration. Such forms include injectable solutions, suppositories, external preparations, ophthalmic solutions, nasal preparations, preparations for administration through catheterization, and other non-oral preparations. These can be produced by a method well known in the art. The nucleoside derivative of the invention and the above-described chimera molecule can also be applied to or used against plant cells as agrochemicals or plant modifiers. In such a case, they can be prepared in the form of tablets, capsules or liquid preparations, for instance, without any particular restriction.

EXAMPLES

The following reference examples and working examples illustrate the invention in more detail. However, these examples and so forth are by no means limitative of the scope of the invention. In the examples, uracil (pyrimidine nucleic acid base) and inosine (purine nucleic acid base) were mainly used as the base (X), and glutamic acid was mainly used as the amino acid or a derivative thereof (Y, Y'). Other nucleic acid bases and amino acids or derivatives thereof can also be used in the same manner.

Reference Example 1

Production of 5'-amino-5'-deoxyuridine (5'-$NH_2$-Urd)

(1) Production of 5'-azido-5'-deoxyuridine

Uridine (5.5 g, 22.5 mmol), triphenylphosphine (11.8 g, 45.0 mmol) and lithium azide (5.51 g, 112.6 mmol) were dissolved in dried DMF (120 ml). Then, carbon tetrabromide (14.92 g, 45.0 mmol) was added with vigorous stirring and after 2 hours of stirring, about 5 ml of methanol was added to terminate the reaction. The DMF was distilled off under reduced pressure, and the residue was purified by column chromatography (silica gel; chloroform-methanol (30:1 v/v) to give 5'-azido-5'-deoxyuridine (5.40 g, 21.2 mmol, yield 94%). A white solid.

vmax (Se board)/$cm^{-1}$: 3370, 2080, 1690, 1270, 1100, 1060 $\delta H$ (270 MHz; DMS-$d_6$): 3.59(2H, m, 5'-H), 3.92(2H, m, 3'-H, 4'-H), 4.13(1H,q,$J_{2',1}=J_{2',3'}$=5.0,2'-H), 5.30(1H,d,$J_{OH,3'}$,5.0,3'-OH), 5.50(1H,d,$J_{OH,2'}$5.6,2'-OH), 5.67(1H,d, $J_{5,6}$ 7.9,5-H), 5.77(1H,d,$J_{1',2}$5.6,1'-H), 7.69(1H,d,$J_{6,5}$7.9,6-H), 11.38(1H,s, 3-NH).

(2) Production of 5'-amino-5'-deoxyuridine

To a solution of the 5'-azido-5'-deoxyuridine (2.51 g, 9.33 mmol) obtained as described above in methanol (100 ml) was added palladium-on-carbon Pd/C (10%, about 0.25 g). While bubbling hydrogen (1 atm), the mixture was stirred at room temperature for 2 hours. Then, the reaction mixture obtained was filtered to remove the palladium-on-carbon, the filtrate was evaporated under reduced pressure, and the residue was reprecipitated from methanol-ethanol to give 5'-amino-5'-deoxyuridine (5'-$NH_2$-Urd) (2.22 g, yield 98%) as powders. A white solid.

vmax (KBr disc)/$cm^{-1}$: 3400, 1680, 1640, 1500, 1460, 1270, 1120, 1050.

$^1$H NMR (270 MHz; DMS-$d_6$): $\delta$ 2.74(2H, m, 5'-H), 3.74(1H, q, $J_{4',3'}=J_{4',5'}$=4.6,4'-H), 3.92(1H, t, $J_{3',2}=J_{3',4'}$=4.8, 3'-H), 4.05(1H, t, $J_{2',1}=J_{2',3'}$=5.5,2'-H), 5.11(4H, br, 2'-OH, 3'-OH, 5'-$NH_2$), 5.62(1H, d, $J_{5,6}$7.8,5-H), 5.75(1H, d, $J_{1',2'}$ 5.6,1'-H), 7.87(1H, d, $J_{6,5}$8.0,6-H).

Found: C, 42.81; H, 5.63; N, 16.98. Calc. for $C_9H_{13}N_3O_5 \cdot 1/2H_2O$: C, 42.86; H, 5.59; N, 16.66%: FAB MS(NBA): m/z 244(M+H).

Reference Example 2

Production of 5'-amino-5'-deoxycytidine (5'-$NH_2$-Cyd)

A suspension of cytidine (9.72 g, 40.0 mmol) in pyridine (200 ml) was added to trimethylchlorosilane (25.6 ml, 200 mmol). After 15 minutes of stirring, benzoyl chloride (23.2 ml, 200 mmol) was added, and the reaction was allowed to proceed at room temperature for 2 hours. The reaction mixture was then cooled on an ice bath, and water (40 ml) was added. Five minutes later, 28% aqueous ammonia (40 ml) was added, and the mixture was stirred at room temperature for 15 minutes. Then, the solvent was distilled off under reduced pressure, and acetone was added to precipitate a white solid. The precipitate was filtered off and recrystallized from water to give $N^4$-benzoylcytidine (13.3 g, 96%). The $N^4$-benzoylcytidine (13.0 g, 37.4 mmol), triphenylphosphine (28.0 g, 107 mmol) and lithium azide (13.0 g, 266 mmol) were suspended in dried DMA, and carbon tetrabromide (35.5 g, 107 mmol) was added to the suspension. After 3 hours of stirring at room temperature, ethyl acetate (1500 ml) was added, and the mixture was washed with water and a saturated aqueous solution of sodium chloride (1000 ml each). The organic layer was dried over magnesium sulfate, and the solvent was evaporated under reduced pressure. The residue was recrystallized from methanol to give 5'-azido-5'-deoxy-N-benzoylcytidine (12.4 g, yield 89%). A solution of 5'-azido-5'-deoxy-$N^4$-benzoylcytidine (10.0 g, 26.9 mmol) in methanol-DMF (1:1 v/v, 100 ml) was vigorously stirred with 10% palladium-on-carbon (about 1.0 g) in a hydrogen atmosphere. The resulting mixture was filtered, and the filtrate was evaporated under reduced pressure to give 5'-amino-5'-deoxy-$N^4$-benzoylcyridine (9.04 g, yield 97%).

Then, the thus-obtained 5'-amino-5'-deoxy-$N^4$-benzoylcytidine (8.5 g, 24.5 mmol) was dissolved in 28% aqueous ammonia (200 ml), and the mixture was stirred at room temperature for 24 hours. The solution was evaporated to dryness, and acetone was added to recover 5'-amino-5'-deoxycytidine (5.76 g, yield 97%).

vmax (KBr disc)/cm$^{-1}$: 3400, 1690, 1660, 1470, 1320, 1220, 1120.

$^1$H NMR (270 MHz; DMSO-d$_6$): δ 2.75(2H, m, 5'-H), 3.71(1H, q, $J_{4',3'}=J_{4',5'}$=4.9,4'-H), 3.86(1H, $J_{3',2'}=J_{3',4'}$=5.4,3'-H), 3.93(1H, $J_{2',1'}=J_{2',3'}$=4.4,2'-H), 4.95(3H, br, 3'-OH, 5'-NH$_2$), 5.25(1H, br, 2'-OH), 5.71(1H, d, $J_{5,6}$7.3,5-H), 5.76 (1H, d, $J_{1',2'}$ 4.4,1'-H), 7.14(1H, br, 4-NH$_2$), 7.77(1H, d, $J_{6,5}$ 7.3,6-H)

Found: C, 44.52; H, 5.79; N, 23.33. Calc. for C$_9$H$_{14}$N$_4$O$_4$: C, 44.63; H, 5.83; N, 23.13%: FAB MS(NBA): m/z 243 (M+H).

Reference Example 3

Production of 5'-amino-5'-deoxyinosine (5'-NH$_2$-Ins)

Inosine (890 mg, 3.0 mmol) was dried under reduced pressure for 1 hour. Thereto was added 1.02 g (21 mmol) of lithium azide, and the mixture was further dried for 1 hour. Distilled DMF (40 ml) was added to the reaction vessel, and the pressure was reduced for about 10 minutes with stirring. Further, 2.20 g (8.4 mmol) of triphenylphosphine was added and, after confirmation of the dissolution of triphenylphosphine, 2.78 g (8.14 mmol) of carbon tetrabromide was added to initiate the reaction. On that occasion, the solution turned yellow. After 8 hours, the completion of the reaction was confirmed by TLC, and the reaction was quenched with methanol. The solution was distilled under reduced pressure, and the residue was purified by silica gel column chromatography (mobile phase MeOH:CHCl$_3$=1:5) to give 5'-azido-5'-deoxyinosine. Isolation yield 775 mg, 88%.

The thus-obtained 5'-azido-5'-deoxyinosine was then dissolved in methanol and reduced with hydrogen for 12 hours using palladium-on-carbon Pd/C (10%, 80 mg) as a catalyst, whereby 5'-amino-5'-deoxyinosine was obtained.

Yield 91%.

$^1$H NMR (270 MHz; DMSO-d$_6$): δ 3.61(m, 2H), 4.10(m, 8H), 4.63(m, 2H), 5.40(d, 1H), 5.63(d, 1H), 5.90(d, 1H), 8.08(s, 1H): IR (KBr) n 1610, 1695 cm$^{-1}$: MS (FAB): m/z 267(M$^+$, 39.4): UV (phosphate buffer) λmax (ε) 258 nm.

Reference Example 4

Production of 5'-amino-5'-deoxythymidine (5'-NH$_2$-Thd)

Thymidine (2.42 g, 10.0 mmol) was dried under reduced pressure for 1 hour. Thereto was added 2.20 g (4.5 eq) of lithium azide, and the mixture was further dried for 1 hour. Distilled DMF (50 ml) was added to the reaction vessel, and the pressure was reduced for about 10 minutes with stirring.

Further, 3.41 g (1.3 eq) of triphenylphosphine was added and, after confirmation of the dissolution of triphenylphosphine, 4.97 g (1.5 eq) of carbon tetrabromide was added to initiate the reaction. On that occasion, the solution turned yellow. After 40 minutes, the completion of the reaction was confirmed by TLC, and the reaction was quenched with methanol. The solution was distilled under reduced pressure, and the residue was purified by silica gel column chromatography (mobile phase MeOH:CHCl$_3$=1:9) to give 5'-azido-5'-deoxythymidine.

$^1$H-NMR (DMSO, 270 MHz): δ 1.79(s, 3H), 2.01–2.32 (m, 2H), 3.56(d,J=5.4 Hz, 2H), 3.83(q,J=Hz, 1H), 4.19(m, 1H), 5.42(d, 4.4 Hz, 1H), 6.20(t, J=6.84 Hz, 1H), 7.50(s, 1H), 11.35(s, 1H).

The thus-obtained 5'-azido-5'-deoxythymidine was then dissolved in methanol and reduced with hydrogen using 10% palladium/carbon as a catalyst, whereby 5'-amino-5'-deoxythymidine was obtained. Yield 1.734 g, 71.6%.

$^1$H-NMR (DMSO, 270 MHz): δ 1.78(s, 3H), 1.96–2.19 (m, 2H), 2.62–2.76(d, J=5.37 Hz, 2H), 3.64(q, 1H), 4.19(m, 1H), 6.14(t,J=6.84 Hz, 1H), 7.66(s, 1H).

Example 1

Poly(N$^γ$-(5'-deoxy-5'-uridyl)-L-glutamine) (PRNA1)

Pentachlorophenyl trichloroacetate (0.454 g, 1.10 mmol) and diisopropylethylamine (0.174 ml, 1.00 mmol) were carefully added to a solution of poly(L-glutamic acid) (0.129 g) in DMF (20 ml) at 0° C. with stirring. After 1 hour, the 5'-amino-5'-deoxyuridine (0.267 g, 1.10 mmol) produced as described in Reference Example 1 was added to the reaction mixture, and the whole mixture was heated at 60° C. for 10 hours. Then, the solvent was removed under reduced pressure, and ethanol was added to the residue to give poly(N$^γ$-(5'-deoxy-5'-uridyl)-L-glutamine) (0.314 g). A white solid.

UV (H$_2$O, pH 7.2) λmax=262 nm (ε=9.8×10$^3$); vmax (KBr disc)/cm$^{-1}$: 3350, 3100, 2900, 1680, 1540,1460, 1390, 1260.

$^1$H NMR (270 MHz; DMSO-d$_6$): δ 1.88(2H, br, β-CH$_2$), 2.15(2H, br, γ-CH$_2$), 3.34(1.81H, br, 5'-H), 3.80(1.85H, m, 3'-H, 4'-H), 4.07(0.92H, br, 2'-H), 4.22(1H, br, α-CH), 5.17(0.93H, s, 3'-OH), 5.40(0.93H, s, 2'-OH), 5.67(0.93H, br, 5-H), 5.72(0.93H, br, 1'-H), 7.65(0.92H, br, 6-H), 8.01 (1.90H, m, α-NH, 5'-NH), 11.33(0.93H, br, 3-NH).

Found: C, 46.97; H, 5.30; N, 13.47. El. Anal. Calcd. for (C$_{14}$H$_{18}$N$_4$O$_7$)$_{0.53}$(C$_5$H$_7$NO$_3$)$_{0.47}$: C, 47.01; H, 5.28; N, 13.48%:

Example 2

PRNA2

A peptide ribonucleic acid (PRNA2) having an oligo(γ-L-glutamic acid) skeleton was produced according to the following reaction formula:

(1) Production of $N^4$-t-butoxycarbonyl-$N^5$-(5'-deoxy-5'-uridyl)-L-isoglutamine benzyl ester (Boc-isoGln(5'U)-OBzl) (Compound 5)

Diisopropylethylamine (1.30 ml. 7.47 mmol) was added to a DMF solution (100 ml) of glutamic acid with its amino terminus protected with a t-butoxycarbonyl group and its carbonyl group with a benzyl ester group, namely N-t-

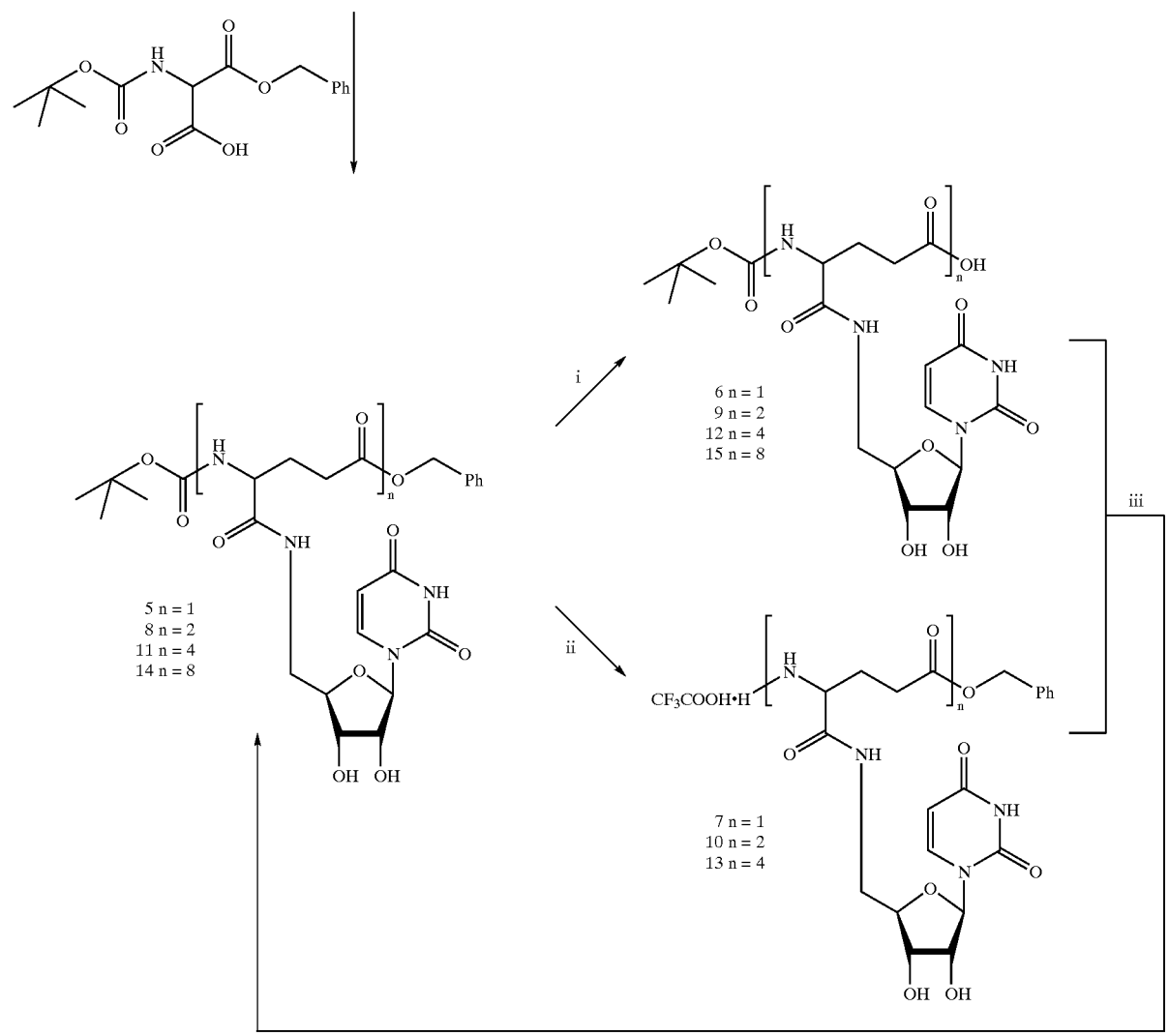

butoxycarbonyl-L-glutamic acid γ-benzyl ester (Boc-isoGln-OBzl) (2.52 g, 7.47 mmol), HOBt (1.01 g, 7.47 mmol) and the BOP reagent (benzotriazol-1-yloxytris (dimethylamino)phosphorium hexafluorophosphate) (3.30 g, 7.47 mmol). After 30 seconds of stirring at 0° C., the 5'-amino-5'-deoxyuridine (1b) (2.00 g, 8.22 mmol) produced in Reference Example 1 was added, and the reaction mixture was stirred at room temperature for 1 hour. After reaction, the solvent was distilled off under reduced pressure, and the residue obtained was suspended in ethyl acetate (200 ml). The suspension was thoroughly washed with an equal volume each of 4% sodium hydrogen carbonate, 5% potassium hydrogen sulfate and a saturated aqueous solution of sodium chloride. The organic layer was dried over magnesium sulfate and filtered, and the filtrate was concentrated under reduced pressure. The residue obtained was purified by column chromatography (solid phase; silica gel, mobile phase: chloroform-methanol (30:1 v/v) to give powdery Boc-isoGln(5'U)-Obzl (compound 5, n=1) (3.70 g, 88%).

νmax (KBr)/cm$^{-1}$: 3420, 1680, 1520, 1460, 1390, 1250, 1170.

$^1$H-NMR (270 MHz; DMSO-d$_6$) δ 1.37(9H, s, t-Bu-H), 1.77–1.88(2H, m, β-CH$_2$), 2.36(2H, t, J$_{γ,β}$=7.8,γ-CH$_2$), 3.29 (2H, m, 5'-H), 3.83(2H, m, 3'-H, 4'-H), 3.94(1H, q, J$_{CH,NH}$=J$_{CH,β}$=7.3, Boc-NHCH), 4.01(1H, q, J$_{2',1'}$=J$_{2',3'}$=5.4,2'-H), 5.07(2H, s, PhCH$_2$), 5.18(1H, d, J$_{OH,3'}$=4.9,3'-OH), 5.40(1H, d, J$_{OH,2'}$=5.4,2'-OH), 5.63(1H, d, J$_{5,6}$8.3,5-H), 5.74(1H, d, J$_{1',2'}$=5.9,1'-H), 6.94(1H, d, J$_{NH,CH}$=7.8,Boc-NH), 7.35(5H, m, Ar—H), 7.64(1H, d, J$_{6,5}$=7.8,6-H), 8.00(1H, t, J$_{NH,5'}$=5.6,5'-NH), 11.35(1H, s, 3-NH),

Found: C, 55.06; H, 6.02; N, 9.76. Calc. for C$_{26}$H$_{34}$N$_4$O$_{10}$·1/4H$_2$O: C, 55.07; H, 6.13; N, 9.88%: MALDI-TOF HRMS (α-CHCA), m/z found 585.220 (M+Na), calculated 585.217.

(2) Production of N$^α$-t-butoxyarbonyl-N$^5$-(5'-deoxy-5'-uridyl)-L-isoglutamine (Boc-isoGln(5'U)-OH (compound 6, n=1), (i)

Palladium-on-carbon (10%, about 0.2 g) was added to a solution of the Boc-isoGln(5'U)-OBzl (1.80 g, 3.20 mmol) (5) obtained as described above in methanol (50 ml). The mixture was continuously stirred in a hydrogen atmosphere (1 atm) for 2 hours, the reaction mixture was then filtered, and the filtrate was evaporated under reduced pressure to give powdery Boc-isoGln(5'U)-OH (1.44 g, yield 95%).

νmax (KBr)/cm$^{-1}$: 3320, 1680, 1530, 1460, 1390, 1250, 1170

$^1$H-NMR (270 MHz; DMSO-d$_6$): δ 1.37(9H, s, t-Bu-H), 1.69–1.82(2H, m, β-CH$_2$), 2.19(2H, t, J$_{γ,β}$=7.3,γ-CH$_2$), 3.29–3.39(2H, m, 5'-H), 3.83(2H, m, 3'-H, 4'-H), 3.92(1H, q, J$_{CH,NH}$=J$_{CH,β}$=5.9,Boc-NHCH), 4.02(1H, t, J$_{2',1'}$=J$_{2',3'}$=4.9, 2'-H), 5.63(1H, d, J$_{5,6}$ 8.3,5-H), 5.73(1H, d, J$_{1',2'}$=5.9,1'-H), 6.92(1H, d, J$_{NH,CH}$=8.3,Boc-NH), 7.65(1H, d, J$_{6,5}$=7.8,6-H), 7.98(1H, t, J$_{NH,5'}$=5.4,5'-NH), 11.35(1H, s, 3-NH), MALDI-TOF HRMS (α-CHCA), m/z found 495.174 (M+Na), calculated 495.170.

(3) Production of N$^5$-(5'-deoxy-5'-uridyl)-L-isoglutamine benzyl ester trifluoroacetate (TFA.isoGln(5'U)-OBzl) (Compound 7, n=1), (ii)

The Boc-isoGln(5'U)-OBzl (1.80 g, 3.20 mmol) obtained as described above under (1) was dissolved in TFA (10 ml), and the solution was allowed to stand at 0° C. for 30 minutes. The TFA was then distilled off under reduced pressure, and 200 ml of ester was added to give powdery TFA.isoGln(5'U)-OBzl (1.81 g, yield 98%).

νmax (KBr)/cm$^{-1}$: 3420, 1680, 1560, 1460, 1270, 1200, 1130

$^1$H-NMR (270 MHz; DMSO-d$_6$): δ 1.97(2H, m,β-CH$_2$), 2.44(2H, t, J$_{γ,β}$=8.1, γ-CH$_2$), 3.82(3H, m, NH$_3^+$CH, 3'-H, 4'-H), 4.11(1H, q, J$_{2',1'}$=J$_{2',3'}$=5.2,2'-H), 5.08(2H, s, PhCH$_2$), 5.24(1H, d, J$_{OH,3'}$=4.9,3'-OH), 5.47(1H, d, J$_{OH,2'}$=5.4,2'-OH), 5.63(1H, d, J$_{5,6}$=8.3,5-H), 5.75(1H, d, J$_{1',2'}$=5.4,1'-H), 7.36(5H, m, Ar—H), 7.66(1H, d, J$_{6,5}$=8.3,6-H), 8.10(3H, br, NH$_3^+$), 8.62(1H, t, J$_{NH,5'}$=5.4,5'-NH), 11.37(1H, s, 3-NH), MALDI-TOF HRMS (α-CHCA), m/z found 463.178(M-CF$_3$COO), calculated 463.183.

(4) Production of a Dimer (Boc-(isoGln(5'U))$_2$-OBzl) (Compound 8), Process (iii)

Diisopropylethylamine (0.97 ml. 5.57 mmol) was added to a DMF solution (50 ml) of the Boc-isoGln(5'U)-OH (compound 6) (1.25 g, 2.65 mmol) obtained in the above process (2), HOBt (0.358 g, 2.65 mmol) and the BOP reagent (1.17 g, 2.65 mmol). After 30 seconds of stirring at 0° C., the TFA.isoGln(5'U)-OBzl (compound 7) (1.68 g, 2.92 mmol) produced in the above process (3) was added, and the reaction mixture was stirred at room temperature for 2 hours. After reaction, the solvent was distilled off under reduced pressure, and the residue obtained was purified by column chromatography (solid phase; silica gel, mobile phase: chloroform-methanol (10:1 v/v) to give powdery Boc-(isoGln(5'U))$_2$-OBzl (compound 8, n=2) (1.70 g, yield 70%).

νmax (KBr)/cm$^{-1}$: 3420, 1680, 1540, 1380, 1270, 1200

$^1$H-NMR (270 MHz; DMSO-d$_6$): δ 1.36(9H, s, t-Bu-H), 1.80(4H, m, β-CH$_2$), 2.15(2H, t, J$_{γ,β}$=7.1γ-CH$_2$), 2.35(2H, t,J$_{γ,β}$=7.8,γ-CH$_2$), 3.83(5H, m, Boc-NHCH, 3'-H and 4'-H), 4.03(2H, q, J$_{2',1'}$=J$_{2',3'}$=4.4,2'-H), 4.26(1H, q, J$_{CH,NH}$=J$_{CH,β}$=7.3,α-CH), 5.06(2H, s, PhCH$_2$), 5.16(2H, s, 3'-OH), 5.39 (2H, d, J$_{OH,2'}$=4.4,2'-OH), 5.62(1H, d, J$_{5,6}$=8.3,5-H), 5.64 (1H, d, J$_{5,6}$=7.8,5-H), 5.73(2H, d, J$_{1',2'}$=5.9,1'-H), 6.85(1H, d, J$_{NH,CH}$=8.3, Boc-NH), 7.35(5H, m, Ar—H), 7.63(1H, d, J$_{6,5}$=7.8,6-H), 7.64(1H, d, J$_{6,5}$=7.8,6-H), 7.95(2H, m, 5'-NH), 8.14(1H, t, J$_{NH,CH}$=10.7, α-NH), 11.33(2H, s, 3-NH); MALDI-TOF HRMS (α-CHCA), m/z found 939.339 (M+Na), calculated 939.335.

(5) Production of a Dimer (Boc-(isoGln(5'U))$_2$-OH) (Compound 9, n=2), Process (i)

Palladium-on-carbon (10%, about 0.1 g) was added to a solution of the Boc-(isoGln(5'U))$_2$-OBzl (0.850 g, 0.927 mmol) (8) obtained as described above in methanol (50 ml). The mixture was continuously stirred in a hydrogen atmosphere (1 bar) for 4 hours, the reaction mixture was then filtered, and the filtrate was evaporated under reduced pressure to give powdery Boc-(isoGln(5'U))$_2$-OH (compound 9) (0.736 g, yield 96%).

νmax (KBr)/cm$^{-1}$: 3390, 1680, 1540, 1470, 1390, 1280

$^1$H-NMR (270 MHz; DMSO-d$_6$): δ 1.37(9H, s, t-Bu-H), 1.67–1.81(4H, m, β-CH$_2$), 2.14(4H, m,γ-CH$_2$), 3.58(4H, m, 5'-H), 3.92(4H, m, 3'-H and 4'-H), 4.03–4.24(3H, m, 2'-H and Boc-NHCH), 4.42(1H, q, J$_{CH,NH}$=J$_{CH,β}$=7.1,α-CH), 5.17–5.39(4H, m, 2'-OH and 3'-OH), 5.67(2H, d, J$_{5,6}$=8.3, 5-H), 5.86(2H, d, J$_{1',2'}$=7.8,1'-H), 6.99(1H, d, J$_{NH,CH}$=8.8, Boc-NH), 7.67(2H, d, J$_{6,5}$=8.8,6-H), 7.88(2H, m, 5'-NH), 8.16(1H, m,α-NH), 11.35(2H,s, 3-NH); MALDI-TOF HRMS (α-CHCA), m/z found 849.293 (M+Na), calculated 849.288.

(6) Production of a Dimer (TFA.isoGln(5'U)$_2$-OBzl) (Compound 10, n=2), (ii)

The Boc-(isoGln(5'U))$_2$-OBzl (compound 8) (0.85 g, 0.927 mmol) obtained as described above under (4) was dissolved in TFA (5 ml), and the solution was allowed to stand at 0° C. for 30 minutes. The TFA was then distilled off under reduced pressure, and 100 ml of ether was added to give powdery TFA.isoGln(5'U)$_2$-OBzl (compound 10) (0.846 g, yield 98%).

νmax (KBr)/cm$^{-1}$: 3420, 1680, 1540, 1470, 1280, 1200, 1140;

¹H-NMR (270 MHz; DMSO-d₆): δ 1.89(4H, m,β-CH₂), 2.25–2.34(4H, m,γ-CH₂), 3.59(4H, m, 5'-H), 3.86(6H, m, NH₃⁺CH,α-CH, 3'-H, 4'-H), 4.11(2H, m, 2'-H), 5.08(2H, s, PhCH₂), 5.20(2H, m, 3'-OH), 5.70(2H, d, $J_{5,6}$=7.8,5-H), 5.77(2H, d, $J_{1',2'}$=5.9,1'-H), 7.36(5H, m, Ar—H), 7.89(1 H, m, 5'-NH), 8.10(4H, m, α-NH, NH₃⁺), 8.56(1H, m, 5'-NH), 11.32(2H,s, 3-NH); MALDI-TOF HRMS (α-CHCA), m/z found 817.296 (M-CF₃COO), calculated 817.301.

(7) Production of a Tetramer (Boc-(isoGln(5'U))₄-OBzl) (Compound 11), Process (iii)

Diisopropylethylamine (0.29 ml. 1.68 mmol) was added to a DMF solution (30 ml) of the dimer Boc-isoGln(5'U)₂-OH (compound 9) (0.662 g, 0.801 mmol) obtained as described above under (5), HOBt (0.108 g, 0.801 mmol) and the BOP reagent (0.354 g, 0.801 mmol). After 30 seconds of stirring at 0° C., the TFA.isoGln(5'U)₂-OBzl (compound 10) (0.82 g, 0.881 mmol) produced as described above under (6) was added, and the reaction mixture was stirred at room temperature for 2 hours. After reaction, the solvent was distilled off under reduced pressure, and the residue obtained was purified by column chromatography (solid phase; silica gel, mobile phase: chloroethanol) to give powdery Boc-(isoGln(5'U))₄-OBzl (compound 11) (1.22 g, yield 94%).

νmax (KBr)/cm⁻¹: 3300, 1680, 1540, 1460, 1390, 1270, 1080;

¹H-NMR (270 MHz; DMSO-d₆): δ 1.37(9H,s,t-Bu-H), 1.71–1.82(8H, m,β-CH₂), 2.14(6H, m, γ-CH₂), 2.35(2H, t, $J_{γ,β}$=7.6, γ-CH₂), 3.26–3.44(8H, m, 5'-H), 3.83(9H, m, Boc-NHC$\underline{H}$, 3'-H and 4'-H), 4.04(4H, m, 2'-H), 4.22(3H, m, α-CH), 5.06(2H, s, PhCH₂), 5.16(4H, d, $J_{OH,3'}$=4.4,3'-OH), 5.39(4H, d, $J_{OH,2'}$=5.4,2'-OH), 5.65(4H, d, $J_{5,6}$=7.3,5-H), 5.73(4H, d, $J_{1',2'}$=3.9,1'-H), 6.87(1H, d, $J_{NH,CH}$=7.8, Boc-NH), 7.35(5H, m, Ar—H), 7.65(4H, d, $J_{6,5}$=8.3,6-H), 7.96 (4H, m, 5'-NH), 8.12(3H, m,α-NH), 11.34(4H, s, 3-NH); MALDI-TOF HRMS (α-CHCA), m/z found: 1647.57 (M+Na), calculated 1647.570.

(8) Production of a Tetramer (Boc-(isoGln(5'U))₄-OH) (Compound 12), Process (i)

Palladium-on-carbon (10%, about 0.1 g) was added to a solution of the Boc-(isoGln(5'U))₄-OBzl (0.600 g, 0.369 mmol) (11) obtained as described above under (7) in methanol-DMF (1:1 v/v. 30 ml). The mixture was continuously stirred in a hydrogen atmosphere (1 bar) for 4 hours, the reaction mixture was then filtered, and the filtrate was evaporated under reduced pressure to give a powdery tetramer, Boc-(isoGln(5'U))₄-OH (compound 12) (0.550 g, yield 97%).

νmax (KBr)/cm⁻¹: 3420, 1680, 1540, 1490, 1380, 1210, 1130;

¹H-NMR (270 MHz; DMSO-d₆): δ 1.37(9H,s,t-Bu-H), 1.69–1.82(8H, m,β-CH₂), 2.15(8H, m,γ-CH₂), 3.85(9H, m,Boc-NHC$\underline{H}$, 3'-H and 4'-H), 4.04(4H, m, 2'-H), 4.20(3H, m, α-CH), 5.21(4H, br, 3'-OH), 5.37(4H, br, 2'-OH), 5.64 (4H, d, $J_{5,6}$=7.8,5-H), 5.73(4H, d, $J_{1',2'}$=5.9,1'-H), 6.87(1H, d, $J_{NH,CH}$=8.3, Boc-NH), 7.65(4H, d, $J_{6,5}$=8.3,6-H), 7.95 (4H, m, 5'-NH), 8.13(3H, m,α-NH), 11.33(4H, s, 3-NH); MALDI-TOF HRMS (α-CHCA), m/z found 1557.52 (M+Na), calculated 1557.523.

(9) Production of a Tetramer (TFA.isoGln(5'U))₄-OBzl (Compound 13), Process (ii)

The Boc-(isoGln(5'U))₄-OBzl (compound 11) (0.600 g, 0.369 mmol) obtained as described above under (7) was dissolved in TFA (5 ml), and the solution was allowed to stand at 0° C. for 30 minutes. The TFA was then distilled off under reduced pressure, and 100 ml of ether was added to give powdery TFA.isoGln(5'U)₄-OBzl (compound 13) (0.593 g, yield 98%).

νmax (KBr)/cm⁻¹: 3420, 1680, 1540, 1460, 1390, 1270, 1130

¹H-NMR (270 MHz; DMSO-d₆): δ 1.76–1.89(8H, m, β-CH₂), 2.13–2.25(6H, m, γ-CH₂), 2.34(2H, t, $J_{γ,β}$=8.3, γ-CH₂), 3.83(9H, m, NH₃⁺CH, 3'-H and 4'-H), 4.05–4.22 (7H, m, α-CH and 2'-H), 5.06(2H, s, PhCH₂), 5.16(3H, m, 3'-OH), 5.24(1H, d, $J_{OH,3'}$=4.9,3'-OH), 5.42(3H, m, 2'-OH), 5.48(1H, d, $J_{OH,2'}$=5.4,2'-OH), 5.64(4H, m, 5-H), 5.73(4H, m, 1'-H), 7.35(5H, m,Ar—H), 7.66(4H, m, 6-H), 7.95(3H, m, 5'-NH), 8.13(6H, m, α-NH and NH₃⁺), 8.61(1H, m, 5'-NH), 11.35(4H, m, 3-NH); MALDI-TOF HRMS (α-CHCA), m/z found 1548.52 (M-CF₃COO+Na), calculated 1548.526.

(10) Production of an Octamer (Boc-(isoGln(5'U))8-OBzl) (Compound 14), Process (iii)

Diisopropylethylamine (0.11 ml. 0.641 mmol) was added to a DMF solution (30 ml) of the tetramer Boc-isoGln(5'U)₄-OH (compound 12) (0.468 g, 0.305 mmol) obtained as described above under (8), HOBt (0.041 g, 0.305 mmol) and the BOP reagent (0.135 g, 0.305 mmol). After 30 seconds of stirring at 0° C., the TFA.isoGln(5'U)₄-OBzl (compound 13) (0.550 g, 0.335 mmol) obtained as described above under (9) was added, and the reaction mixture was stirred at room temperature for 4 hours. After reaction, the solvent was distilled off under reduced pressure, and methanol was added to the residue, whereby a powdery octamer, Boc-(isoGln(5'U))₈-OBzl (compound 14) (0.854 g, yield 92%) was obtained.

νmax (KBr)/cm⁻¹: 3420, 1680, 1530, 1460, 1400, 1270, 1130;

¹H-NMR (270 MHz; DMSO-d₆): δ 1.37(9H,s,t-Bu-H), 1.71–1.82(16H, m,β-CH₂), 2.14(14H, m, γ-CH₂), 2.34(2H, t, $J_{γ,β}$=7.8, γ-CH₂), 3.25–3.42(16H, m, 5'-H), 3.83(17H, m,Boc-NHC$\underline{H}$, 3'-H and 4'-H), 4.05(8H, m, 2'-H), 4.20(7H, m,α-CH), 5.06(2H, s, PhCH₂), 5.15(8H, d, $J_{OH,3'}$=3.4,3'-OH), 5.39(8H, d, $J_{OH,2'}$=5.4,2'-OH), 5.64(8H, d, $J_{5,6}$=7.8,5-H), 5.73(8H, d, $J_{1',2'}$=5.4,1'-H), 6.87(1H, d, $J_{NH,CH}$=7.3, Boc-NH), 7.35(5H, m,Ar—H), 7.64(8H, d, $J_{6,5}$=7.8,6-H), 7.95(8H, m, 5'-NH), 8.13(7H, m,α-NH), 11.33(8H,s, 3-NH); MALDI-TOF HRMS (α-CHCA), m/z found 3064.04 (M+Na), calculated 3064.041.

(11) Production of an Octamer(Boc-(isoGln(5'U))₈OH) (Compound 15), Process (i)

Palladium-on-carbon (10%, about 0.1 g) was added to a solution ot the octamer (Boc-(isoGln(5'U) )₈-Obzl) (compound 14) (0.800 g, 0.263 mmol) obtained as described above under (10) in methanol-DMF (1:3 v/v, 50 ml). The mixture was continuously stirred in a hydrogen atmosphere (1 bar) for 6 hours, the reaction mixture was then filtered, and the filtrate was evaporated under reduced pressure to give powdery Boc-(isoGln(5'U))₈-OH (compound 15) resulting from elimination of the C-terminal protective group benzyl (0.745 g, yield 96%).

νmax (KBr)/cm⁻¹: 3410, 1680, 1540, 1470, 1390, 1260, 1110

¹H-NMR (270 MHz; DMSO-d₆): δ 1.37(9H,s,t-Bu-H), 1.70–1.82(16H, m, β-CH₂), 2.15(16H, m, γ-CH₂), 3.83 (17H, m, Boc-NHC$\underline{H}$, 3'-H and 4'H), 4.05(8H, m, 2'-H), 4.19(7H, m,α-CH), 5.18(8H, m, 3'-OH), 5.29(8H, m, 2'-OH), 5.65(8H, d, $J_{5,6}$=7.8,5-H), 5.73(8H, d, $J_{1',2'}$=5.9,1'-H), 6.88(1H, d, $J_{NH,CH}$=8.8, Boc-NH), 7.65(8H, d, $J_{6,5}$=8.3, 6-H), 7.95(8H, m, 5'-NH), 8.14(8H, m,α-NH), 11.33(8H, s, 3-NH); MALDI-TOF HRMS (α-CHCA), m/z found 2973.99 (M+Na), calculated 2973.994.

Example 3

A PRNA2 having a free N terminus was prepared according to the following reaction formula:

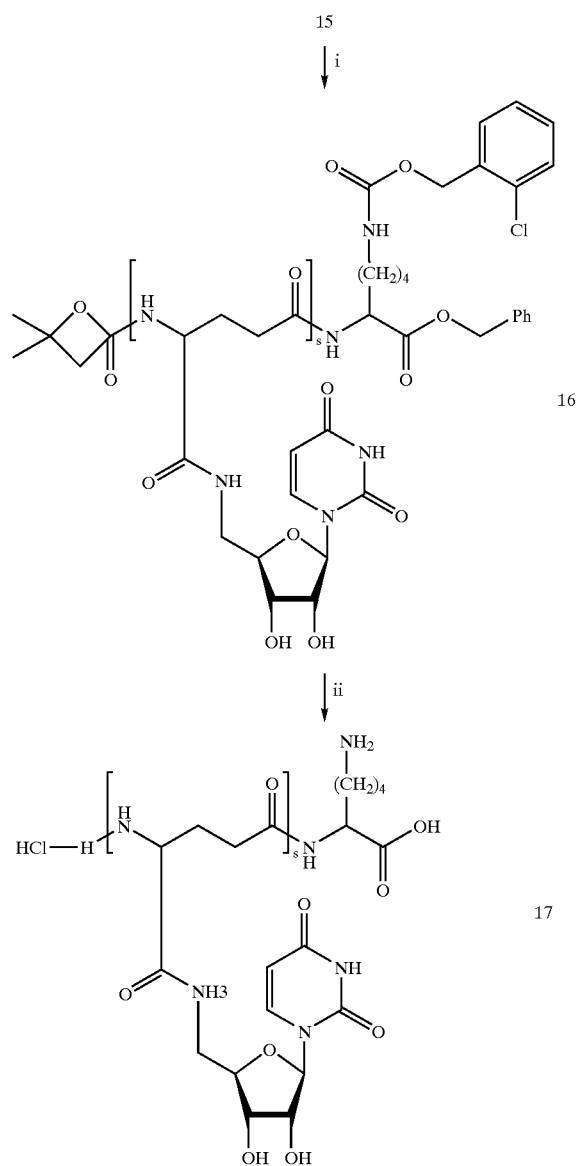

(1) Production of Boc-(isoGln(5'U))₈-Lys(CIZ)-Bzl (Compound 16), Process (i)

Diisopropylethylamine (0.04 ml. 0.237 mmol) was added to a DMF solution (30 ml) of the octamer Boc-(isoGln (5'U))₈-OH (compound 15) (0.700 g, 0.237 mmol obtained in Example 2 (11), HOBt (0.032 g, 0.237 mmol) and the BOP reagent (0.105 g, 0.237 mmol). After 30 seconds of stirring at 0° C., N$^{ϵ-2}$-chlorobenzyloxycarbonyl-O-benzyl-L-lysine (0.106 g, 0.261 mmol) was added, and the mixture was stirred at room temperature for 4 hours. After reaction, the solvent was distilled off under reduced pressure, and methanol was added to the residue, whereby powdery Boc-(isoGln(5'U))₈-Lys(CIZ)-Bzl (compound 16) (0.712 g, yield 90%) was obtained.

vmax (KBr)/cm$^{-1}$: 3330, 1680, 1540, 1470, 1390, 1270, 1130

$^1$H-NMR (270 MHz; DMSO-d₆): δ 1.36(13H, m,t-Bu-H, γ-CH₂(Lys) and δ-CH₂(Lys)), 1.57–1.84(18H, m, β-CH₂ (Glu) and β-CH₂(Lys)), 2.14(16H, m, β-CH₂(Glu)), 2.98 (2H, m, ϵ-CH₂(Lys)), 3.83(17H, m, Boc-NHC$\underline{H}$, 3'-H and 4'-H), 4.05(8H, m, 2'-H), 4.20(8H, m, α-CH), 5.07(2H, s, PhCH₂), 5.08(2H, s, Cl-PhCH₂), 5.16(8H, d, J$_{OH,3'}$=3.9,3'-OH), 5.39(8H, d, J$_{OH,2'}$=5.4,2'-OH), 5.65(8H, d, J$_{5,6}$=7.8,5-H), 5.73(8H, d, J$_{1',2'}$=5.9,1'-H), 6.87(1H, d, J$_{NH,CH}$=7.3, Boc-NH), 6.99(1H, m, ϵ-NH(Lys)), 7.35(5H, m, Ar—H (Bzl)), 7.45(4H, m, Ar—H(Cl-Z)), 7.65(8H, d, J$_{6,5}$=7.8,6-H), 7.96(8H, m, 5'-NH), 8.14(8H, m, α-NH), 11.33(8H, s, 3-NH); MALDI-TOF HRMS (α-CHCA), m/z found 3360.13 (M+Na), calculated 3360.134.

(2) Production of HCl.(isoGln(5'U))₈-Lys-OH (Compound 17), Process (ii)

The Boc-(isoGln(5'U))₈-Lys(CIZ)-Bzl (Compound 16) (0.300 g, 0.090 mmol) obtained as described above under (1) was dissolved in TFA (10 ml), and the solution was stored at −10° C. in a nitrogen atmosphere. Thioanisole (1.84 ml, 15.7 mmol), m-cresol (0.97 ml, 9.27 mmol) and trimethylsilyl triflate (3.00 ml, 16.6 mmol) were added in that order, and the mixture was stirred at 0° C. for 1 hour. Ether (200 ml) was added, and the resulting precipitate was filtered off and dissolved in 5% aqueous ammonia. After 30 minutes, the solvent was distilled off under reduced pressure, and the residue was treated with 4 M hydrochloric acid in dioxane for 30 minutes, The solvent was distilled off, and the residue was purified by gel filtration and reversed phase HPLC to give powdery HCl.(isoGln(5'U))₈-Lys-OH (compound 17) (0.223 g, yield 82%).

vmax (KBr)/cm$^{-1}$: 3420, 1680, 1540, 1460, 1390, 1270, 1110;

$^1$H-NMR (270 MHz; DMSO-d₆): δ 1.35(4H, m,γ-CH₂ (Lys), δ-CH₂(Lys)), 1.70–1.83(16H, m, β-CH₂(Glu)), 2.14 (16H, m, γ-CH₂(Glu)), 2.98(2H, m,ϵ-CH₂(Lys)), 3.84(17H, m, NH₃$^+$CH, 3'-H and 4'-H), 4.06(8H, m, 2'-H), 4.20(8H, m,α-CH), 5.17(8H, m, 3'-OH), 5.41(8H, m, 2'-OH), 5.65 (8H, d, J$_{5,6}$=7.8,5-H), 5.73(8H, d, J$_{1',2'}$=5.9,1'-H), 7.24(2H, br, ϵ-NH₂), 7.65(8H, d, J$_{6,5}$=7.8,6-H), 7.95(7H, m, 5'-NH), 8.14(11H, m, α-NH and NH₃$^+$), 8.59(1H, m, 5'-NH), 11.34 (8H, m, 3-NH); MALDI-TOF HRMS (α-CHCA), m/z found 2980.86 (M-HCl), calculated 2980.055.

Example 4

Production of Boc-AEG(5'U)-OBn Oligomer (PRNA3)

(1) Production of Boc-AEG-OBn

Boc-AEG-OBn was produced according to the following reaction formula:

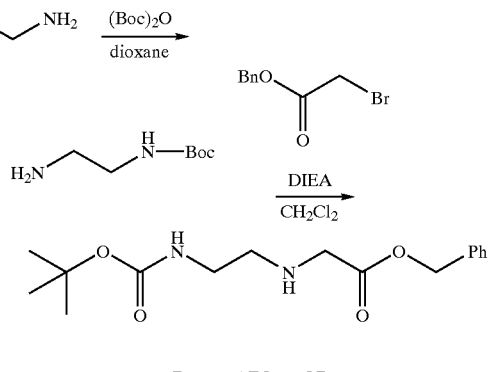

Boc—AEG—OBn

① Synthesis of N-Boc-1,2-aminoethane

To a solution of ethylenediamine (52.5 g, 874 mmol) in dioxane (300 ml) was added dropwise with stirring a di-tertbutyl dicarbonate ((Boc)$_2$O) in dioxane (300 ml) over 10 hours. After the dropping, stirring was continued for 24 hours. After completion of the reaction, the dioxane was distilled off under reduced pressure, and 400 ml of water was added to the residue. The insoluble matter was removed by filtration, and the aqueous layer was extracted with chloroform (500 ml×4). The organic layers were combined and dried over magnesium sulfate. After drying, the filtrate was concentrated under reduced pressure and purified by column chromatography (silica gel; chloroform-methanol (10:1 v/v) to give N-Boc-1,2-aminoethane (14.6 g, 91.4 mmol, yield 81% (based on Boc$_2$O). A white solid.

② Synthesis of Boc-AEG-OBn

The N-Boc-1,2-aminoethane (4.64 g, 29.0 mmol) and diisopropylethylamine (4.50 g, 34.8 mmol) were dissolved in chloroform (40 ml), and a solution of benzyl bromoacetate (6.57 g, 28.7 mmol) in chloroform (30 ml) was added dropwise thereto with stirring over 1 hour. After completion of the dropping, stirring was continued for 24 hours. The solvent was distilled off under reduced pressure, and the residue was purified by column chromatography (silica gel; ethyl acetate alone) to give Boc-AEG-OBn (7.00 g, 22.7 mmol, yield 79%). A colorless liquid.

δH (270 MHz; DMSO-d$_6$): 1.31(9H,s,t-Bu-H), 2.49(2H, t, J6.6, BocNHCH$_2$—CH$_2$), 2.92(2H, m,Boc-NH—CH$_2$), 3.31 (2H, s, CH$_2$—COOBn), 5.06(2H, s, Ph-CH), 6.67(1H,br, Boc-NH), 7.26–7.31(5H, m, Ar—H).

(2) Production of Boc-AEG(5'U)-OBn

Boc-AEG(5'U)-OBn was produced according to the following reaction formula:

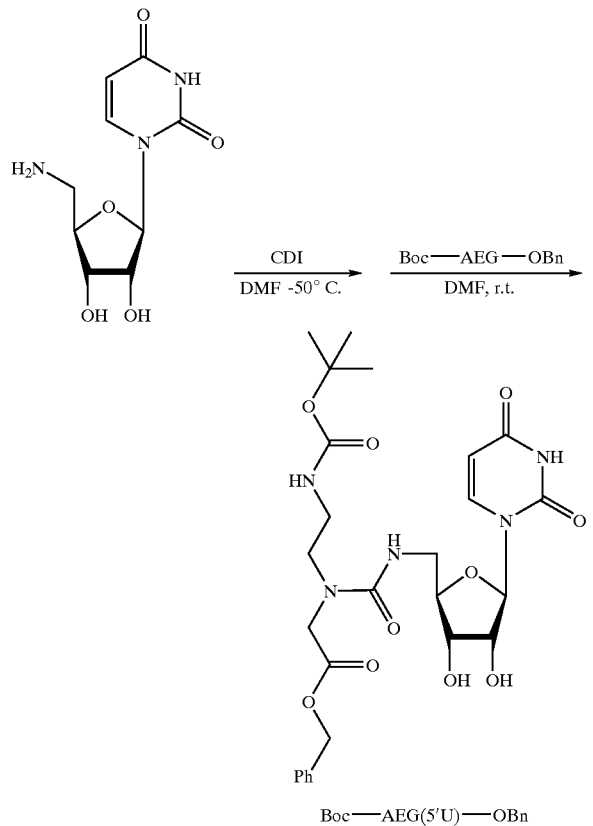

The 5'-amino-5'-deoxyuridine (5'-NH$_2$-Urd) (1.80 g, 7.40 mmol) prepared in Reference Example 1 was dissolved in dried DMF (50 ml), and a solution of CDI (1.14 g, 7.04 mmol) in DMF (40 ml) was added dropwise with stirring at −50° C. over 1 hour. The reaction system was stirred at −50° C. for 30 minutes, then the Boc-AEG-OBn (1.72 g, 7.40 mmol) produced as described above was added, and the mixture was stirred at room temperature for 2 days. After completion of the reaction, the DMF was distilled off under reduced pressure at room temperature, and the residue was purified by column chromatography (silica gel; chloroform-methanol (20:1 v/v)) to give Boc-AEG(5'U)-OBn (2.64 g, 4.58 mmol, yield 65%). A white solid.

νmax (KBr)/cm$^{-1}$: 3380, 1690, 1540, 1460, 1390, 1250, 1170

δH(270 MHz; DMSO-d$_6$): 1.35(9H, s, t-Bu—H), 2.9–3.1 (2H, m, Boc-NHCH), 3.2–3.4(4H, m, BocNHCH$_2$-CH$_2$,5'-H), 3.85(1H, q, 4'-H), 3.89(1H, q, 3'-H), 4.01(1H, q, 2'-CH), 4.06(2H, s, CH$_2$COOBn), 5.08(1H, d, $J_{3'\text{-}OH,3'\text{-}H}$,4.9,3'-OH), 5.11(2H, s, Ph—CH$_2$), 5.35(1H, d, $J_{2'\text{-}OH,2'\text{-}H}$5.7,2'-OH), 5.60(1H, d, $J_{5,6}$ 10.5,5-H), 5.70(1H, d, $J_{1',2'\text{-}H}$ 5.4.5,1'-H), 6.65(1H, br, 5'-NH), 6.77(1H, br, Boc-NH), 7.31–7.36(5H, m, Ar—H), 7.64(1H, d, $J_{6,5}$ 7.8,6H), 11.33(1H, s, 3-NH); m/z (FAB) 600 (M+Na)$^+$.

(3) Production of Boc-AEG(5'U)-OH

Palladium-on-carbon (Pd/C, 10 wt % Pd, 0.02 g) was added to a methanol solution (30 ml) of the Boc-AEG(5'U)-OBn (0.2 g, 0.35 mmol) obtained as described above, and the reaction was allowed to proceed while bubbling hydrogen with stirring for 1 hour. After completion of the reaction, the Pd/C was filtered off, and the filtrate was concentrated under reduced pressure. The residue was recrystallized from methanol-ethanol to give Boc-AEG(5'U)-OH (0.16 g, 0.33 mmol, yield 95%). A white solid. νmax (KBr)/cm$^{-1}$: 3390, 1690, 1540, 1460, 1400, 1250, 1170 δH(270 MHz; DMSO-d$_6$): 1.35(9H, s, t-Bu-H), 3.01(2H, m, Boc-NHCH$_2$), 3.15–3.33(4H, m, Boc-NHCH$_2$-CH$_2$,5'-H$_2$), 3.78–3.82(2H, m, HN—CO, 4'-H), 3.89–3.91(3H, m, 3'H, CH$_2$COOH), 3.98–4.00(1H, m, 2'-H), 5.07(1H, br, 3'-OH), 5.32(1H, d, $J_{2'\text{-}OH,2'\text{-}H}$5.0,2'-OH), 5.62(1H, d, $J_{5,6}$ 8.4,5-H), 5.62(1H, d, $J_{1',2'\text{-}H}$ 5.9,1'-H), 6.57(1H, br, 5'-NH), 6.77(1H, t, $J_{Boc\text{-}NH,5'}$4.7, Boc-NH), 7.63(1H, d, $_{6,5}$ 8.1,6-H), 11.32(1H,s, 3-NH); m/z (FAB) 510 (M+Na)$^+$.

(4) Process for Producing TFA.AEG(5'U)-OBn

The Boc-AEG(5'U)-OBn obtained as described above under (2) was dissolved in TFA, and the solution was allowed to stand at 0° C. for 30 minutes. The TFA was then distilled off under reduced pressure, and ester was added, whereby TFA.AEG(5'U)-OBn was obtained.

(5) Oligomer Production

A dimer, Boc-(AEG(5'U))$_2$-OBn is prepared using the Boc-AEG(5'U)-OH and TFA.AEG(5'U)-OBn prepared as described above and following the process of Example 2 (4). Further, oligomers can be prepared according to the processes of Example 2 (5) to (11).

Example 5

(1) Production of a Trimer (Boc-(isoGln(5'U))$_3$-OBzl)

The Boc-(isoGln(5'U))$_4$-OH (compound 9) (343 mg, 0.37 mmol) obtained in Example 2 (5), HOBt (56 mg, 1 eq) and the BOP reagent (184 mg, 1 eq) were dissolved in distilled DMF at 0° C., and the solution was stirred for about 1 hour until returning to room temperature. To this solution was added diisopropylethylamine (DIEA) (131 mg, 2 eq), and the TFA.isoGln(5'U)-OBzl (compound 7) (251 mg, 1 eq) obtained in Example 2 (3) was then added, and the mixture was stirred at room temperature for 2 hours. After reaction, the solvent was evaporated under reduced pressure, and the residue was reprecipitated from ethanol to give the trimer Boc-(isoGln(5'U))$_3$-OBzl. Yield 200 mg, 37.9%.

¹H-NMR (270 MHz; DMSO): δ 1.36(s, 9H), 1.58–1.92 (m, 6H), 2.14(t, 3H), 2.34(t, 3H), 3.74–3.94(m, 7H), 3.98–4.10(m, 3H), 4.15–4.30(m, 2H), 5.06(s, 2H), 5.20(m, 3H), 5.40(m, 3H), 5.63(m, 3H), 5.73(d, 3H), 6.90(d, 1H), 7.35(m, 5H), 7.65(d, 3H), 7.98(m, 3H), 8.15(m, 2H), 11.35 (s, 3H).

(2) Production of a Trimer (Boc-(isoGln(5'U))$_3$-OH)

The Boc-(isoGln(5'U))$_3$-OBzl (200 mg) obtained as described above was dissolved in methanol, and palladium-on-carbon (10%, about 40 mg) was added. The reaction was allowed to proceed in a hydrogen atmosphere for about 2 hours, followed by reprecipitation with ether to give Boc-(isoGln(5'U))$_3$-OH. Yield 190 mg, 91%.

¹H-NMR (270 MHz; DMSO): δ 1.36(s, 9H), 1.59–1.90 (m, 6H), 2.07–2.30(m, 6H), 3.73–3.93(m, 6H), 3.99–4.09 (m, 3H), 4.13–4.30(m, 2H), 5.05–5.48(m, 4H), 5.58–5.77 (m, 6H), 6.90(d, 1H), 7.61–7.71(m, 3H), 7.93–8.22(m, 5H), 11.35(s, 3H) UV (phosphate buffer) λmax (ε) 262 nm.

Example 6

Purine Base Type (Inosine)-Nucleoside Derivative (1) Production of N$^4$-t-butoxycarbonyl-N$^5$-(5'-deoxy-5'-inosyl)-L-isoglutamine benzyl ester (Boc-isoGln(5'I)-OBzl)

N-t-Butoxycarbonyl-L-glutamine γ-benzyl ester (Boc-L-Glu(OBzl)) (1.32 g, 3.9 mmol), HOBt (526 mg, 1 eq) and the BOP reagent (1.747 g, 1 eq) were dissolved in distilled DMF at 0° C., and the mixture was stirred for about 1 hour until returning to room temperature. DIEA (613 mg, 1 eq) was added to this solution, the 5'-amino-5'-deoxyinosine (1.04 g, 1 eq) prepared in Reference Example 3 was then added, and the mixture was stirred at room temperature for about 2 hours. The solvent was evaporated under reduced pressure and the residue was purified by silica gel column chromatography (MeOH:CHCl$_3$=1:9) to give Boc-isoGln(5'I)-OBzl. Yield 1.56 g, 68%.

¹H-NMR (270 MHz; DMSO): δ 1.33(s, 9H), 1.82(m, 8H), 2.35(t, 2H), 3.38(m, 2H), 3.97(m, 3H), 4.54(q, 1H), 5.05(s, 1H), 5.31(d, 1H), 5.48(d, 1H), 5.83(d, 1H), 6.96(d, 1H), 7.34(m, 5H), 8.07(t, 1H), 8.12(s, 1H), 8.30(s, 1H): IR (KBr) n 1610, 1695 cm⁻¹: MS (FAB) m/z 587 (M⁺, 39.4): UV (phosphate buffer) λmax (ε) 258 nm.

(2) Production of N$^α$-t-butoxycarbonyl-N$^5$-(5'-deoxy-5'-inosyl)-L-isoglutamine (Boc-isoGln(5'I)-OH)

The Boc-isoGln(5'I)-OBzl (1.09 g, 1.86 mmol) obtained as described above under (1) was dissolved in methanol, palladium-on-carbon (about 40 mg) was added, and the reaction was allowed to proceed in a hydrogen atmosphere for about 2 hours to give Boc-isoGln(5'I)-OH. Yield 900 mg, 97.5%.

¹H-NMR (270 MHz; DMSO): δ 1.33(s, 9H), 1.82(m, 8H), 2.35(t, 2H), 3.38(m, 2H), 3.97(m, 3H), 4.54(q, 1H), 5.31(d, 1H), 5.48(d, 1H), 5.83(d, 1H), 6.96(d, 1H), 8.07(t, 1H), 8.12(s, 1H), 8.30(s, 1H). UV (phosphate buffer) λmax(ε) 249 nm.

(3) Production of N$^5$-(5'-deoxy-5'-inosyl)-L-isoglutamine benzyl ester trifluoroacetate (TFA.isoGln(5'I)-OBzl)

The Boc-isoGln(5'I)-OBzl (1.01 g, 1.72 mmol) obtained as described above under (1) was dissolved in TFA, and the reaction was allowed to proceed at 0° C. for 2 hours. The TFA was then distilled off under reduced pressure, and ether was added to the residue to give TFA.isoGln(5'I)-OBzl. Yield 1.03 mg, 99%.

¹H-NMR (270 MHz; DMSO): δ 1.97(dd, 2H), 2.43(t, 2H), 3.38(m, 2H), 3.81(m, 3H), 4.11(q, 4H), 4.54(q, 1H), 5.08(s, 2H), 5.31(d, 1H), 5.48(d, 1H), 5.83(d, 1H), 6.96(d, 1H), 7.36(m, 5H), 8.07(t, 1H), 8.12(s, 1H), 8.30(s, 1H).

(4) Production of a Dimer (Boc-(isoGln(5'I))$_2$-OBzl)

The Boc-isoGln(5'I)-OH (182 mg, 0.37 mmol) obtained as described above under (2), HOBt (50 mg, 1 eq) and the BOP reagent (162 mg, 1 eq) were dissolved in distilled DMF at 0° C., and the mixture was stirred for about 1 hour until returning to room temperature.

Diisopropylethylamine (DIEA) (115 mg, 2 eq) was added to this solution, the TFA.isoGln(5'I)-OBzl (220 mg, 1 eq) prepared in (3) was then added, and the mixture was stirred at room temperature for about 2 hours. After reaction, the solvent was distilled off under reduced pressure, and the residue obtained was purified by column chromatography (mobile phase: MeOH:AtOEc=1:2) to give the dimer Boc-(isoGln(5'I))$_2$-OBzl (yield 320 mg, 78%).

¹H-NMR (270 MHz; DMSO): δ 1.31(s, 9H), 1.59–1.97 (m, 4H), 2.15(t, 2H), 2.33(t, 2H), 3.82–4.05(m, 2H), 4.21–4.32(q, 1H), 4.56(t, 2H), 5.03(d, 1H), 5.50(bloaded-s, 1H), 5.82(d, 2H), 6.93(d, 1H), 7.33(m, 5H), 7.97–8.23(m, 7H) UV (phosphate buffer) λmax (ε) 248 nm.

(5) Production of a Dimer (Boc-(isoGln(5'I))$_2$-OH)

The Boc-(isoGln(5'I))$_2$-OBzl (320 mg) obtained as described above under (4) was dissolved in methanol, and palladium-on-carbon (10%, about 40 mg) was added. The reaction was allowed to proceed in a hydrogen atmosphere for about 2 hours to give Boc-(isoGln(5'I))$_2$-OH (yield 298 mg, 88%).

¹H-NMR (270 MHz; DMSO): δ 1.31(s, 9H), 1.59–1.97 (m, 4H), 2.15(t, 2H), 2.33(t, 2H), 3.82–4.05(m, 2H), 4.21–4.32(q,1H), 4.56(t, 2H), 5.50(bloaded-s, 1H), 5.82(d, 2H), 6.93(d, 1H), 7.97–8.23(m, 7H); UV (phosphate buffer) λmax (ε) 248 nm.

Example 7

Pyrimidine-Purine Mixed Sequence-Containing PRNAs (1)

(1) Production of a Dimer (Boc-isoGln(5'U)-isoGln(5'I)-OBzl)

The Boc-isoGln(5'U)-OH (compound 6) (945 mg, 2.0 mmol) obtained in Example 2 (2), HOBt (270 mg, 1 eq) and the BOP reagent (890 mg, 1 eq) were dissolved in distilled DMF at 0° C., and the mixture was stirred for about 1 hour until returning to room temperature. Diisopropylethylamine (DIEA) (0.74 mg, 2 eq) was added to this solution, the TFA-isoGln(5'I)-OBzl (1.32 g, 1 eq) prepared in Example 6 (3) was then added, and the mixture was stirred at room temperature for about 2 hours. After reaction, the solvent was distilled off under reduced pressure, and the residue obtained was purified by silica gel column chromatography (mobile phase: MeOH:AtOEc=1:9) to give Boc-isoGln (5'U)-isoGln(5'I)-OBzl (yield 1.86 g, 97.2%).

¹H-NMR (270 MHz; DMSO): δ 1.35(s, 9H), 1.79(m, 4H), 2.15(m, 2H), 2.33(t, 2H), 3.76–4.13(m, 7H), 4.27(q, 1H), 4.55(q, 1H), 5.04(s, 2H), 5.17(d, 1H), 5.39(d, 1H), 5.51(d, 1H), 5.61(d, 1H), 5.73(d, 1H), 5.83(d, 1H), 6.87(d, 1H), 73.4(m, 5H), 7.64(d, 1H), 7.91–8.05(m, 2), 8.11(s, 1H), 8.31(s, 1H); MS(FAB) m/z 941 (M⁺, 12.1).

(2) Production of a Dimer (Boc-isoGln(5'U)-isoGln(5'I)-OH)

The Boc-isoGln(5'U)-isoGln(5'I)-OBzl (527 mg, 0.56 mmol) prepared as described above under (1) was dissolved in methanol, and palladium-on-carbon (10%, about 40 mg) was added. The reaction was allowed to proceed in a hydrogen atmosphere for about 2 hours to give Boc-isoGln (5'U)-isoGln(5'I)-OH (yield 466 mg, 98%).

¹H-NMR (270 MHz; DMSO): δ 1.36(s, 9H), 1.58–1.91 (m, 4H), 2.05–2.27(m, 4H), 3.74–4.07(m, 6H), 4.24(q, 1H), 4.55(t, 1H), 5.08–5.59(m, 3H), 5.64(d, 1H), 5.73(d, 1H), 5.83(d, 1H), 6.88(d, 1H), 7.65(d, 1H), 7.90–8.25(m, 4), 8.31(s, 1H), 11.34(s, 1H); UV (phosphate buffer) λmax (ε) 258 nm.

(3) Production of a Dimer (TFA-isoGln(5'U)-isoGln(5'I)-OBzl)

The Boc-isoGln(5'U)-isoGln(5'I)-OBzl obtained as described above under (1) was dissolved in TFA, and the reaction was allowed to proceed at 0° C. for 2 hours. The TFA was then distilled off under reduced pressure, and ether was added to the residue to give TFA.isoGln(5'U)-isoGln(5'I)-OBzl. Yield 798 mg, 98%.

$^1$H-NMR (270 MHz; DMSO): δ 1.97(m, 2H), 2.38–2.48 (m, 2H), 3.43–4.55(m, 1H), 3.74–3.88(m, 3H), 4.11(q, 1H), 5.08(s, 2H), 5.27(d, 1H), 5.49(d, 1H), 5.63(d, 1H), 5.75(d, 1H), 7.36(m, 5H), 7.66(d, 1H), 8.10(bloaded-s, 3), 8.64(t, 1H), 11.39(s, 1H).

(4) Production of a Tetramer (Boc-isoGln((5'U)-isoGln(5'I))$_2$-OBzl)

The Boc-isoGln(5'U)-isoGln(5'I)-OH (160 mg, 0.19 mmol) prepared as described above under (2), HOBt (25.4 mg, 1 eq) and the BOP reagent (83.3 mg, 1 eq) were dissolved in distilled DMF at 0° C., and the mixture was stirred for about 1 hour until returning to room temperature. DIEA (59.1 mg, 2 eq) was added to this solution, the TFA.isoGln(5'U)-isoGln(5'I)-OBzl (179 mg, 1 eq) prepared as described above under (3) was then added, and the mixture was stirred at room temperature for about 2 hours. After reaction, the solvent was evaporated under reduced pressure, and the residue was dissolved in methanol and reprecipitated with ether to give Boc-isoGln((5'U)-isoGln(5'I))$_2$-OBzl (yield 260 mg, 82.6%).

$^1$H-NMR (270 MHz; DMSO): δ 1.35(s, 9H), 1.79(m, 8H), 2.15(m, 4H), 2.33(t, 4H), 3.76–4.13(m, 14H), 4.27(q, 2H), 4.55(q, 2H), 5.04(s, 2H), 5.17(m, 2H), 5.39(m, 2H), 5.51(m, 2H), 5.64(m, 2H), 5.73(m, 2H), 5.83(m, 2H), 6.87(m, 2H), 7.34(m, 5H), 7.64(d, 2H), 7.91–8.05(m, 4), 8.11(s, 2H), 8.31(s, 2H); MS (TOP) m/z 1674 (M$^+$).

(5) Production of a Tetramer (Boc-isoGln((5'U)-isoGln(5'I))$_2$-OH)

The Boc-isoGln((5'U)-isoGln(5'I))$_2$-OBzl (334 mg, 0.2 mmol) prepared as described above under (4) was dissolved in methanol, and palladium-on-carbon (10%, about 40 mg) was added. The reaction was allowed to proceed in a hydrogen atmosphere for about 2 hours to give Boc-isoGln((5'U)-isoGln(5'I))$_2$-OH (yield 288 mg, 91%).

$^1$H-NMR (270 MHz; DMSO): δ 1.36(s, 9H), 1.58–1.91 (m, 8H), 2.05–2.27(m, 8H), 3.74–4.07(m, 12H), 4.24(q, 2H), 4.55(t, 2H), 5.08–5.59(m, 6H), 5.64(d, 2H), 5.73(d, 2H), 5.83(d, 2H), 6.88(d, 2H), 7.65(d, 2H), 7.90–8.25(m, 8), 8.31(s, 2H), 11.34(s, 2H); UV (phosphate buffer) λmax(ε) 258 nm.

(6) Production of a Tetramer (TFA-isoGln((5'U)-isoGln(5'I))$_2$-OBzl

The Boc-isoGln((5'U)-isoGln(5'I))$_2$-OBzl (334 mg, 0.2 mmol) prepared as described above under (4) was dissolved in TFA, and the reaction was allowed to proceed at 0° C. for 2 hours. The TFA was then distilled off under reduced pressure, and ether was added to the residue for reprecipitation, whereby TFA.isoGln((5'U)-isoGln(5'I))2-OBzl was obtained. Yield 290 mg, 92%.

$^1$H-NMR (270 MHz; DMSO): δ 1.95(m, 4H), 2.38–2.50 (m, 4H), 3.42–4.45(m, 2H), 3.75–3.87(m, 6H), 4.11–4.14(q, 2H), 5.08(s, 4H), 5.27(m, 2H), 5.49(d, 2H), 5.63(m, 2H), 5.75(m, 2H), 7.36(m, 5H), 7.66(d, 2H), 8.10(bloaded-s, 6), 8.64(t, 2H), 11.39(s, 2H)

(7) Production of an Octamer (Boc-isoGln((5'U)-isoGln(5'I))$_4$-OBzl)

The Boc-isoGln((5'U)-isoGln(5'I))$_2$-OH (65 mg, 4.1× 10$^{-5}$ mol) prepared as described above under (5), HOBt (5.5 mg, 1 eq) and the BOP reagent (18.2 mg, 1 eq) were dissolved in distilled DMF at 0° C., and the mixture was stirred for about 1 hour until returning to room temperature. DIEA (12.9 mg, 2 eq) was added to this solution, the TFA.isoGln((5'U)-isoGln(5'I))$_2$-OBzl (69.2 mg, 1 eq) prepared as described above under (6) was then added, and the mixture was stirred at room temperature for about 2 hours. After reaction, the solvent was evaporated under reduced pressure, and the residue was dissolved in DMF, followed by reprecipitation with ethanol to give Boc-isoGln((5'U)-isoGln(5'I))$_4$-OBzl (yield 113 mg, 88.0%).

$^1$H-NMR (270 MHz; DMSO): δ 1.35(s, 9H), 1.57–1.96 (m, 16H), 2.13(m, 14H), 2.33(t, 4H), 3.74–4.32(m, 28H), 4.56(m, 4H), 5.03(s, 2H), 5.17(m, 4H), 5.30(m, 4H), 5.40(m, 4H), 5.53(m, 4H), 5.63(d, 2H), 5.66(d, 2H), 5.72(m, 4H), 5.83(m, 4H), 6.89(m, 1H, 7.32(m, 5H), 7.59–7.70(m, 5H), 7.84–8.35(m, 4), 11.32(s, 4H); MS (TOP) m/z 3139 (M$^+$).

Example 8

Pyrimidine-purine Mixed Sequence-containing PRNAs (2)

(1) Production of a Dimer (Boc-isoGln(5'I)-isoGln(5'U)-OBzl)

The Boc-isoGln(5'I)-OH (520 mg, 1.05 mmol) prepared in Example 6 (2), HOBt (142 mg, 1 eq) and the BOP reagent (465 mg, 1 eq) were dissolved in distilled DMF at 0° C., and the mixture was stirred for about 1 hour until returning to room temperature. DIEA (330 mg, 2 eq) was added to this solution, the TFA.isoGln(5'U)-OBzl (605 mg, 1 eq) prepared in Example 2 (3) was then added, and the mixture was stirred at room temperature for about 2 hours. After reaction, the solvent was evaporated under reduced pressure, and the residue obtained was purified by silica gel column chromatography (mobile phase: MeOH:AtOEc=1:9) to give Boc-isoGln(5'I)-isoGln(5'U)-OBzl (yield 652 mg, 66.0%).

$^1$H-NMR (270 MHz; DMSO): δ 1.35 (s, 9H), 1.79(m, 4H), 2.15(m, 2H), 2.33(t, 2H), 3.76–4.13(m, 7H), 4.27(q, 1H), 4.55(q, 1H), 5.04(s, 2H), 5.17(d, 1H), 5.39(d, 1H), 5.51(d, 1H), 5.64(d, 1H), 5.73(d, 1H), 5.83(d, 1H), 6.87(d, 1H), 7.34(m, 5H), 7.64(d, 1H), 7.91–8.05(m, 2), 8.11(s, 1H), 8.31(s, 1H); MS (FAB) m/z 941 (M$^+$, 10.9).

(2) Production of a Dimer (Boc-isoGln(5'I)-isoGln(5'U)-OH)

The Boc-isoGln(5'I)-isoGln(5'U)-OBzl (527 mg, 0.56 mmol) prepared as described above was dissolved in methanol, and palladium-on-carbon (10%, about 40 mg) was added. The reaction was allowed to proceed in a hydrogen atmosphere for about 2 hours to give Boc-isoGln(5'I)-isoGln(5'U)-OH (yield 410 mg, 91%).

$^1$H-NMR (270 MHz; DMSO): δ 1.36(s, 9H), 1.58–1.91 (m, 4H), 2.05–2.27(m, 4H), 3.74–4.07(m, 6H), 4.24(q, 1H), 4.55(t, 1H), 5.08–5.59(m, 3H), 5.64(d, 1H), 5.73(d, 1H), 5.83(d, 1H), 6.88(d, 1H), 7.65(d, 1H), 7.90–8.25(m, 4), 8.31(s, 1H), 11.34(s, 1H); UV (phosphate buffer) λmax(ε) 259 nm.

Example 9

Production of a Trimer (Boc-isoGln(5'U)-isoGln(5'I)-isoGln(5'U)-OBzl)

The Boc-isoGln(5'U)-isoGln(5'I)-OH (80 mg, 0.094 mmol) prepared in Example 7 (2), HOBt (12.7 mg, 1 eq) and the BOP reagent (41.6 mg, 1 eq) were dissolved in distilled DMF at 0° C., and the mixture was stirred for about 1 hour until returning to room temperature. DIEA (30 mg, 2 eq) was added to this solution, the TFA.isoGln(5'U)-OBzl (54.2 mg, 1 eq) prepared in Example 2 (3) was then added, and the mixture was stirred at room temperature for about 2 hours. After reaction, the solvent was evaporated under reduced pressure, and the residue obtained was dissolved in DMF and reprecipitated with methanol/ether to give the trimer Boc-isoGln(5'U)-isoGln(5'I)-isoGln(5'U)-OBzl (yield 98 mg, 88.0%).

$^1$H-NMR (270 MHz; DMSO): δ 1.36(s, 9H), 1.60–1.95 (m, 8H), 2.05–2.20(m, 4H), 2.33, (t, 2H), 3.74–4.08(m, 9H), 4.22(m, 2H), 4.57(q, 1H), 5.05(s, 2H), 5.14–5.20(m, 2H), 5.29(d, 1H), 5.40(m, 2H), 5.52(d, 1H), 5.61(d, 1H), 5.65(d, 1H), 5.73(d, 2H), 5.83(d, 2H), 6.90(d, 1H), 7.34(m, 5H), 7.64(d,2H), 7.92–8.04(m,3H), 8.09–8.24(m, 3H), 8.32(s, 1H), 11.35(s, 1H); MS (FAB) m/z 1295 (M$^+$, 2.4).

Example 10

Solid Phase Synthesis of Nucleoside Derivatives (PRNA (γ Type) Oligomers)

(1) Production of an Fmoc-PRNA Monomer (γ Type)

(i) N$^α$-9-fluorenylmethoxycarbonyl-N$^5$-5'-deoxy-5'-uridinyl-L-isoglutamine benzyl ester (Fmoc-isoGln(5'U-OBzl)

The TFA.isoGln(5'U)-OBzl (compound 7) (2.196 g, 3.81 mmol) prepared in Example 2 (3) and Fmoc-Osu (N-(9-fluorenylcarbonyloxy)succinimide) (1.537 g, 1.2 eq) were dissolved in distilled DMF at 0° C., and the solution was stirred. DIEA (1.99 g, 2 eq) was added to this solution, and the mixture was stirred at room temperature for 30 minutes. This solution was concentrated under reduced pressure, methanol was added to cause crystallization of Fmoc-isoGln (5'U)-OBzl, and the crystals were recovered. Yield 2.156 g, 82.8%.

$^1$H-NMR (270 MHz; DMSO): δ 1.86(m, 2H), 2.37(t, 2H), 3.83(m, 2H), 4.03(m, 3H), 4.16–4.31(m, 3H), 5.07(s, 2H), 5.22(d, 1H), 5.44(d, 1H), 5.61(d, 1H), 5.74(d, 2H), 7.26–7.44(m,9H), 7.55–7.76(d, 4H), 7.88(d, 2H), 8.14(t, 3H), 11.34(s, 1H).

(ii) N$^α$-9-Fluorenylmethoxycarbonyl-N$^5$-5'-deoxy-5'-uridinyl-L-isoglutamine (Fmoc-isoGln(5'U)-OH)

The Fmoc-isoGln(5'U)-OBzl (2.156 g, 3.15 mmol) obtained as described above under (i) was dissolved in methanol/DMF (1:1), and palladium-on-carbon (10%, about 40 mg) was added. The reaction was allowed to proceed in a hydrogen atmosphere for about 20 minutes to give Fmoc-isoGln(5'U)-OH. This was further purified by reprecipitation with ether. Yield 2.08 g, 99%.

$^1$H-NMR (270 MHz; DMSO): δ 1.86(m, 2H), 2.37(t, 2H), 3.83(m, 2H), 4.03(m, 2H), 4.16–4.31(m, 2H), 5.22(d, 1H), 5.44(d, 1H), 5.61(d, 1H), 5.74(d, 2H), 7.26–7.44(m, 4H), 7.54–7.77(d, 4H), 7.88(d, 2H), 8.15(t, 3H), 11.35(s, 1H).

(iii) N$^α$-9-Fluorenylmethoxycarbonyl-N$^5$-5'-deoxy-5'-inosinyl-L-isoglutamine benzyl ester (Fmoc-isoGln(5'I)-OBzl)

The TFA.isoGln(5'I)-OBzl (910 mg, 1.51 mmol) prepared in Example 6 (3) and Fmoc-Osu (611 mg, 1.2 eq) were dissolved in distilled DMF at 0° C., and the solution was stirred. DIEA (475 mg, 2 eq) was added to this solution, and the mixture was stirred at room temperature for 2 hours. This solution was concentrated under reduced pressure, and the residue was purified by silica gel column chromatography (MeOH:CHCl$_3$=1:9). Yield 943.8 mg, 87.7%.

$^1$H-NMR (270 MHz; DMSO): δ 1.72–2.01(m, 2H), 2.15 (t, 2H), 2.37(t, 2H), 3.25–3.52(m, 6H), 3.91–4.09(m, 3H), 4.55(q, 1H), 5.06(s, 2H), 5.35(d, 1H), 5.53(d, 1H), 5.84(d, 1H), 7.25–7.44(m, 9H), 7.63(d, 1H), 7.72(t, 2H), 7.88(d, 2H), 8.10(s, 1H), 8.20(t, 1H), 8.33(s, 1H).

(iv) N$^α$-9-Fluorenylmethoxycarbonyl-N$^5$-5'-deoxy-5'-inosinyl-L-isoglutamine (Fmoc-isoGln(5'I)-OH)

The Fmoc-isoGln(5'I)-OBzl (943.8 mg, 1.32 mmol) obtained as described above under (iii) was dissolved in methanol/DMF (1:1), and palladium-on-carbon (10%, about 40 mg) was added. The reaction was allowed to proceed in a hydrogen atmosphere for about 2 hours to give Fmoc-isoGln(5'I)-OH. This was further purified by reprecipitation from ether. Yield 880 mg, 93.2%.

$^1$H-NMR (270 MHz; DMSO): δ 1.65–1.96(m, 2H), 2.23 (t, 2H), 3.32–3.50(m, 3H), 3.90–4.08(m, 3H), 4.15–4.30(m, 3H), 4.55(t, 1H), 5.83(d, 1H), 7.26–7.46(m, 4H), 7.64(d, 1H), 7.68–7.78(m, 2H), 7.88(d, 2H), 8.10(s, 1H), 8.20(t, 1H), 8.33(s, 1H).

(2) Production of PRNA Oligomers (FIG. 1)

PRNA oligomers were produced according to the scheme shown in FIG. 1. The solid phase support resin used was NovaSyn (registered trademark) TGR-Resin (product of Pharmacia) having a polyethylene glycol chain as a spacer.

① Preparation of the Solid Phase Support Resin

First, the solid phase support resin with the amino group protected with an Fmoc group was thoroughly swelled with N-methylpyrrolidone (NMP) and, then, the protective group Fmoc was eliminated from the solid phase support resin by reacting with 20% piperidine (PPD)/NMP for 15 minutes. The mixture was stirred on a vortex at 5-minute intervals and, after completion of the reaction, the resin was washed with 5 portions of NMP.

② PRNA Extension Reaction

The PRNA extension reaction was carried out by successive condensation of Fmoc-PRNAs having an Fmoc protective group at the N terminus and a free C terminus by repeating the following reaction.

<Condensation Reaction>

An Fmoc-PRNA (3 eq relative to the resin), 2-(1H-benzotriazol-1-yl)-1,1,3,3-tetramethyluronium hexafluorophosphate (HBTU) (3 eq) and 1-hydroxybenzotriazole (HOBt) (3 eq) were dissolved in NMP, the solution was introduced into a column packed with the above resin, diisopropylethylamine (DIEA) (6 eq) was added, and the reaction was allowed to proceed for 20 minutes with stirring on a vortex at 5-minute intervals. After completion of the reaction, the resin was washed with 5 portions of NMP.

<Reaction Confirmation Test>

The coupling or non-coupling of the Fmoc-PRNA monomer was confirmed by the Kayser test (100° C., 2 minutes) using the ninhydrin reagent capable of reacting with a free amino group. When the test was found positive (when the unreacted amino group was found remaining), the above condensation reaction was again carried out and, if necessary, repeated until completion of the reaction.

The above condensation reaction and reaction confirmation test were conducted alternately to thereby cause the desired Fmoc-PRNA monomers to be involved in the chain extension one by one to synthesize the desired PRNA oligomer on the solid phase support resin.

③ Isolation and Purification of the Synthetic PRNA Oligomer From the Resin

After synthesis, the N terminus of the PRNA oligomer was deprotected by treatment with 20% PPD/NMP, and the resin was washed with 5 portions of NMP. After further washing with 5 portions of chloroform, the resin was dried under vacuum. Then, the synthetic PRNA oligomer was excised-from the resin using TFA containing 5% of water as a scavenger. The TFA was distilled off using an evaporator. While the TFA solution was passed through a column, cold ether was added to precipitate a white solid. This was separated by centrifugation, the supernatant was removed by decantation, and the residue was dried under vacuum to give the PRNA oligomer in a crude form. The crude product was subjected to analytical HPLC under the conditions specified below for confirmation of its giving a single peak, followed by MALDI-TOF for molecular weight determination. Further, the crude product was applied to a preparative column, the desired fraction was recovered, the thus-obtained fraction solution was lyophilized to give a white solid.

<HPLC Conditions>

Analytical column

Nakalai COSMOSIL 4.6×150 mm Type waters, 1 mL/min

Preparative column:

Nakalai COSMOSIL 10×250 mm Type waters, 3 mL/min

Eluent Solution A: 0.1% TFA/water

Eluent Solution B: 0.08% TFA/acetonitrile

Mobile phase:

Adjusted so that the solutions A:solution B ratio might change from 100:0 to 0:100 in 30 minutes.

Detection: UV detection at the wavelength 260 nm.

(2-1) PRNA Oligomer Production (i) The initial coupling reaction onto the solid phase support resin was carried out using lysine with the N terminus protected by a 9-fluorenylmethoxycarbonyl group and the C terminus protected by a benzyl ester group (Fmoc-Lys(OBzl)-OH) as the above-mentioned Fmoc-PRNA monomer, and the subsequent condensation reactions were carried-out using the Fmoc-isoGln(5'U)-OH and Fmoc-isoGln(5'I)-OH prepared in Example 10 (1) (ii) and (iv), respectively to synthesize the following octamer PRNA.

① NH$_2$-Lys-isoGln(5'U)-isoGln(5'U)-isoGln(5'U)-isoGln(5'U)-isoGln(5'U)-isoGln(5'I)-isoGln(5'I)-isoGln(5'U)-OH (PRNA oligomer 1). Yield 88%, TOF-MS m/z=3021.8 (M$^+$).

Figure 2:
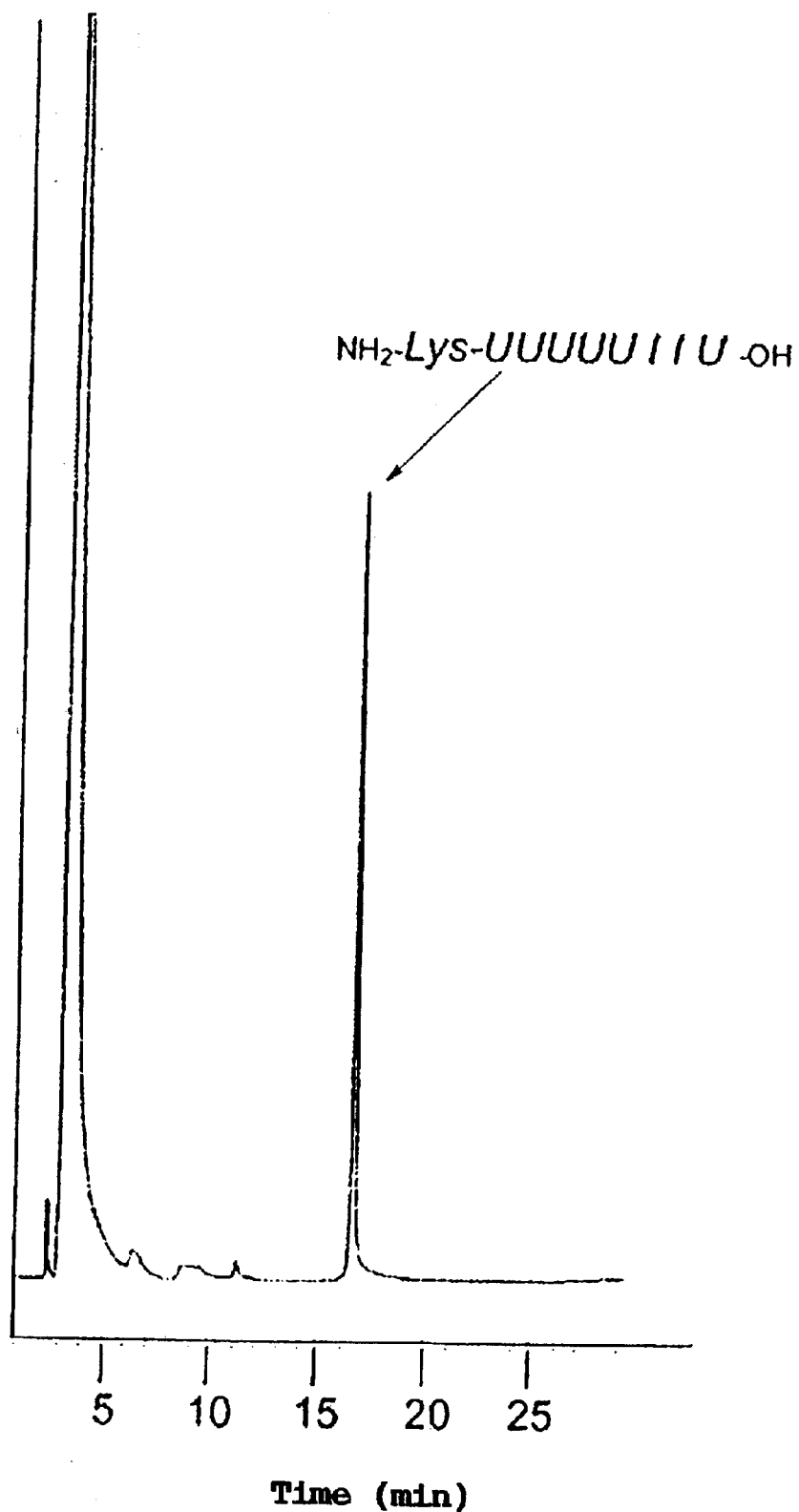
FIG. 2 is a chromatogram showing the results of HPLC analysis of the PRNA oligomer 1 produced (synthesized on a solid phase) in Example 10.

The results of HPLC analysis are shown in FIG. 2.

(ii) The condensation/extension reaction was repeated using the above Fmoc-isoGln(5'U)-OH and Fmoc-isoGln(5'I)-OH as the above-mentioned Fmoc-PRNA monomers, and the final condensation reaction was carried out using Fmoc-Lys(OBzl)-OH. The following two octamer PRNAs were thus synthesized.

NH$_2$-isoGln(5'U)-isoGln(5'I)-isoGln(5'I)-isoGln(5'U)-isoGln(5'U)-isoGln(5'U)-isoGln(5'U)-isoGln(5'U)-Lys-OH (PRNA oligomer 2), yield 80%, TOF-MS m/z=3021.8(M$^+$). NH$_2$-isoGln(5'I)-isoGln(5'I)-isoGln(5'I)-isoGln(5'I)-isoGln(5'I)-isoGln(5'I)-isoGln(5'I)-isoGln(5'I)-Lys-OH (PRNA oligomer 3), yield 85%, TOF-MS m/z=3165.9(M$^+$).

Example 11

Production of a Chimeric Molecule Dimer (PRNA (Urd)-DNA(Thd))

A chimeric nucleic acid (PRNA(Urd)-DNA(Thd) dimer) was synthesized according to the following scheme using a PRNA having uracil as a base and a DNA having thymine as a base.

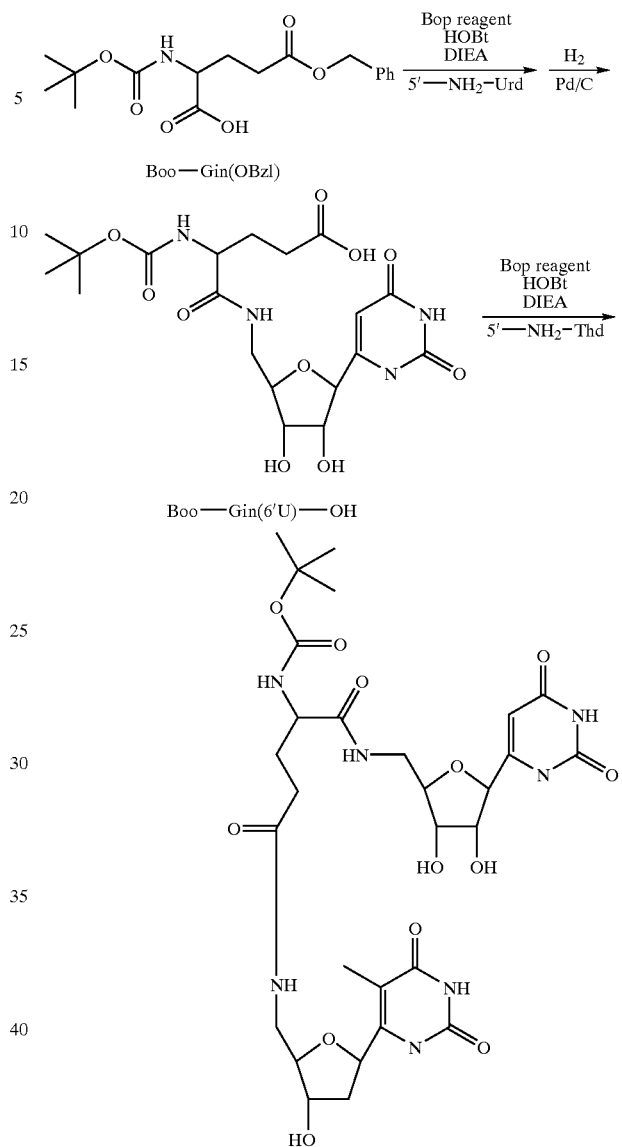

Boc-isoGln(5'U)-OH was synthesized (yield 88%) by introducing 5'-NH$_2$-Urd (Reference Example 1) into the α-carboxyl group of N$^4$-t-butoxycarboyl-N$^5$-(5'-deoxy-5'-uridyl)-L-isoglutamine benzyl ester (Boc-isoGln(OBzl)) with use of BOP reagent and HOBt according to the method of Example 2 (1) and, then, deprotecting the γ-carboxyl group in the manner of catalytic reduction according to Example 2 (2). Then, Boc-isoGln(5'U)-OH (326 mg, 0.5 mmol), HOBt (67.5 mg, 1 eq) and the BOP reagent (222 mg, 1 eq) were dissolved in distilled DMF at 0° C., and the solution was stirred for about 1 hour until returning to room temperature. Diisopropylethylamine (DIEA) (97 mg, 1.5 eq) was added to this solution. The 5'-NH$_2$-Thd (424 mg, 1.05 eq) prepared in Reference Example 4 was added, and the mixture was stirred at room temperature for about 3 hours. After confirmation of completion of the reaction by TLC, the reaction was quenched with methanol. This solution was concentrated under reduced pressure, 5 ml of methanol was added, and ether was added to the solution for causing reprecipitation, whereby the title compound PRNA(Urd)-DNA(Thd) was obtained. Yield 332 mg, 95%.

¹H-NMR (270 MHz; DMSO): δ 1.59–1.91(m, 5H), 1.98–2.21(m, 4H), 3.12–3.54(m, 4H), 3.65–4.16(m, 6H), 5.18(d,J=4.9,1H), 5.29(d,J=3.9,1H), 5.40(d,J=5.4 Hz, 1H), 5.64(d,J=8.3 Hz, 1H), 5.73(d,J=5.9 Hz, 1H), 6.13(t,J=1H), 6.89(d,J=8.3,1H), 7.50(s, 1H), 7.64(d,J=7.8 Hz, 1H), 7.90–8.04(m, 2H), 11.30(s, 2H) 7.50.

Example 12

Production of a Chimeric Molecule Dodecamer (PRNA(Urd)$_8$-DNA(Thd)$_4$)

(1) 5'-O-(4,4'-Dimethoxytrityl)thymidine (5'-DMTr-Thd)

Thymidine (1.918 g, 8.0 mmol) was dried under reduced pressure for a while, pyridine was then added in an argon atmosphere, and the mixture was stirred. 4,4'-Dimethoxytrityl chloride (DMTr-Cl) was added at 0° C., and the mixture was allowed to return to room temperature over about 2 hours with stirring. After confirmation of completion of the reaction by TLC, the reaction was quenched with water. This solution was concentrated under reduced pressure, the concentrate was dissolved in dichloromethane, and the solution was washed with a saturated aqueous solution of copper sulfate and with brine. The organic layer was evaporated under reduced pressure, and the residue was purified by silica gel chromatography (MeOH:CH$_2$Cl$_2$=1:9). The eluate fraction was evaporated under reduced pressure, and the residue was dissolved in a small amount of ethyl acetate. Hexane was added to this solution for reprecipitation to give the title compound 5'-DMTr-Thd. Yield 3.67 g, 82.7%.

¹H-NMR (270 MHz; DMSO): δ 1.44(s, 3H), 2.07–2.32 (m, 2H), 3.09–3.26(m, 2H), 3.73(s, 6H), 3.91–3.83(m, 1H), 4.25–4.36(m, 1H), 5.34(d, J=4.4 Hz, 1H), 6.20(t, J=6.84 Hz, 1H), 6.89(d,J=8.3 Hz, 4H), 7.17–7.42(m, 9H), 7.51(s, 1H), 11.35(s, 1H)

(3) 5'-O-(4,4'-Dimethoxytrityl)thymidine 3'-(cyanoethyl N,N-diisopropylphosphoramidite) (5'-DMTr-3'-CEDIPA-Thd)

The 5'-DMTr-Thd (136 mg, 0.25 mmol) prepared as described above under (1) was dried under reduced pressure for a while, dichloromethane was added in an argon atmosphere, and the mixture was stirred. DIPA (17 mg, 0.5 eq) and tetrazole (9 mg, 0.5 eq) were added to this solution and, after dissolution, cyanoethyl N,N'-bis(diisopropyl) phosphorodiamidite (83 mg, 1.1 eq) was added, and the mixture was stirred at room temperature for 3 hours. After confirmation of completion of the reaction by TLC, the reaction was quenched with methanol. This solution was evaporated under reduced pressure, the residue was dissolved in dichloromethane, and the solution was washed with a 5% aqueous solution of sodium hydrogen carbonate and with brine. This organic phase was evaporated under reduced pressure, and the residue was purified by silica gel chromatography (MeOH:CH$_2$Cl$_2$=1:20). The eluate fraction was evaporated under reduced pressure, the residue was dissolved in 5 ml of dichloromethane, and hexane was added to the solution for reprecipitation, whereby 5'-DMTr-3'-CEDIPDA-Thd was obtained. The formation of said compound was confirmed by the occurrence of the base moiety 5-position methyl group, of the sugar moiety 1' hydrogen and of the DMTr group and by the agreeing Rf value. Yield 61.2 mg, 32.2%. Rf (EtOH:CH$_2$Cl$_2$:(Et)$_3$N=50:45:5) 0.49, 0.53.

(3) 5'-N-(4,4'-Dimethoxytrityl)-5'-amino-5'-deoxythymidine (5'-DMTr-NH-Thd)

The 5'-amino-5'-deoxythymidine (5'-NH$_2$-Thd) (241 mg, 1.0 mmol) prepared in Reference Example 4 was dried under reduced pressure for a while and, in an argon atmosphere, pyridine was added, and the mixture was stirred. Thereto was added, at 0° C., 4,4'-dimethoxytrityl chloride (DMTr-Cl) (423.25 mg, 1.25 eq), and the mixture was stirred for about 2 hours while allowing the same to return to room temperature. After confirmation of completion of the reaction by TLC, the reaction was quenched with water. This solution was concentrated under reduced pressure, the residue was dissolved in dichloromethane, and the solution was washed with a saturated aqueous solution of copper sulfate and with brine. This organic phase was evaporated under reduced pressure, and the residue was purified by silica gel chromatography (MeOH;CH$_2$Cl$_2$=1:9). The eluate fraction was evaporated under reduced pressure, and the residue was dissolved in a small amount of ethyl acetate. Hexane was added to this solution for reprecipitation to give the title compound 5'-DMTr-NH-Thd. The formation of said compound was confirmed by the occurrence of the base moiety position 5 methyl group, the sugar moiety position 1' hydrogen and the DMTr group, and through the proton ratio. Yield 203 mg, 37.3%.

(4) 5'-N-(4,4'-Dimethoxytrityl)-5'-amino-5'-deoxythymidine-3'-(cyanoethyl N,N-diisopropylphosphoramidite) (5'-DMTr-NH-3'-CEDIPA-Thd)

The 5'-DMTr-NH-Thd prepared in (3) (393 mg, 0.72 mmol) was dried under reduced pressure for a while and, in an argon atmosphere, dichloromethane was added, and the mixture was stirred. To this solution was added DIEA (187 mg, 2.0 eq) and, after dissolution, cyanoethyl N,N'-diisopropyl chlorophosphorodiamidite (188 mg, 1.1 eq) was added, and the mixture was stirred at room temperature for 3 hours. After confirmation of completion of the reaction by TLC, the reaction was quenched with methanol. This solution was evaporated under reduced pressure, the residue was dissolved in dichloromethane, and the solution was washed with a 5% aqueous solution of sodium hydrogen carbonate and with brine. This organic phase was evaporated under reduced pressure, and the residue was purified by silica gel chromatography (MeOH:CH$_2$Cl$_2$=1:20). The eluate fraction was evaporated under reduced pressure, and the residue was dissolved in 5 ml of dichloromethane. Hexane was added to this solution for reprecipitation to give the title compound 5'-DMTr-NH-3'-CEDIPA-Thd. The formation of said compound was confirmed based on the NMR and Rf data. Yield 293 mg, 54.6%; Rf (EtOH:CH$_2$Cl$_2$:(Et)$_3$N=50:45:5) 0.49, 0.53.

(4) Production of a chimeric molecule (PRNA(Urd)$_8$-DNA (Thd)$_4$)

A chimeric molecule (PRNA(Urd)$_8$-DNA(Thd)$_4$) was synthesized according to the following scheme.

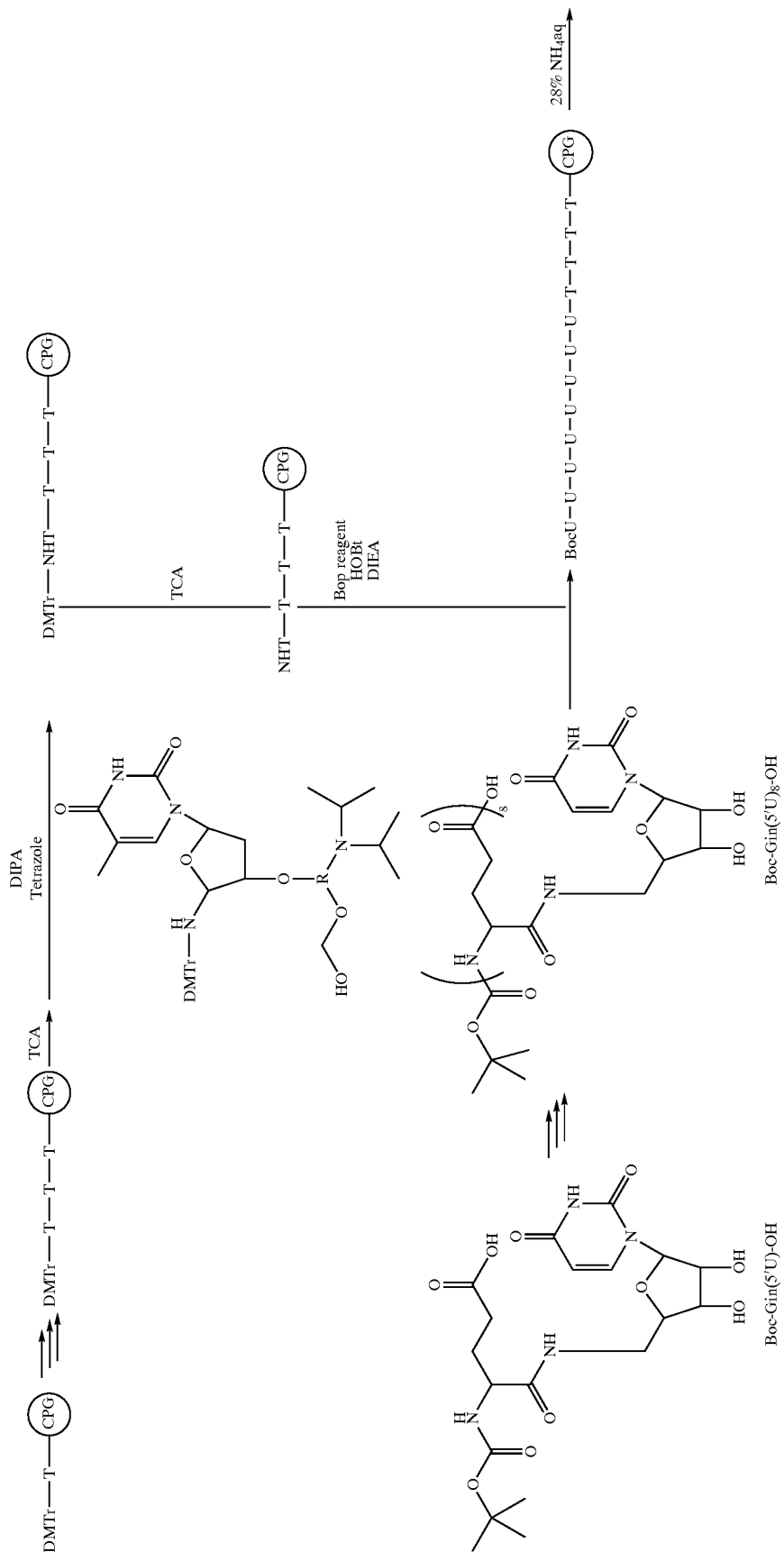

-continued
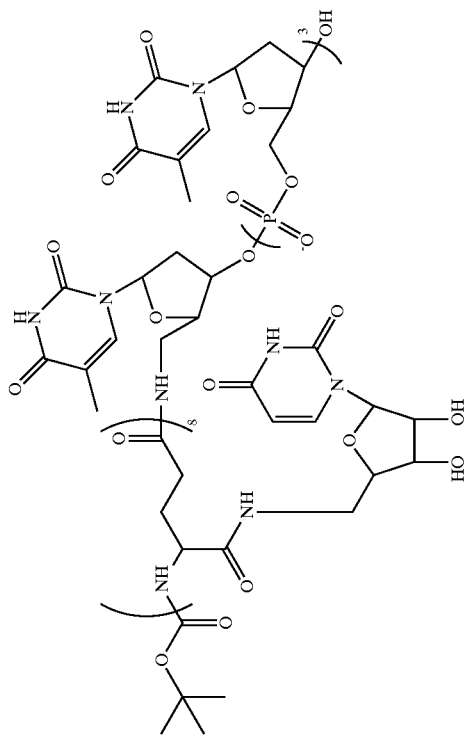
Boc-Gln(5'U)₈-NHT-T₃(U₈T₄)

(i) Solid Phase Synthesis of a DNA Oligomer

First, the 5'-hydroxyl group of thymidine was protected with a 4,4'-dimethoxytrityl chloride (DMTr-Cl) group by the method described above under (1) to give 5'-DMTr-Thd, which was then reacted with cyanoethyl N,N'-bis (diisopropyl)chlorophosphorodiamidite (CEDIPA) in the presence of DIPA and tetrazole, as described above under (2), to give an 3'-amidite derivative of thymidine (5'-DMTr-3'-CEDIPA-Thd). Using a CPG (controlled pored glass) as a solid phase support and while activating with DIPA and tetrazole, the above 3'-amidite derivative of thymidine (5'-DMTr-3'-CEDIPA-Thd) was successively introduced onto the solid phase to extend thymidine on the solid phase to give a trimer. Then, the amino-terminal DMTr-Cl group was eliminated using TCA, and the thymidine trimer formed on the solid phase was condensed with the 3'-amidite derivative of 5'-aminothymidine (5'-DMTr-NH-3'-CEDIPA-Thd) synthesized as described above under (3) and (4) by activating with DIPA and tetrazole, followed again by deprotection with TCA. Thus, a thymidine tetramer having an amino group at the 5' terminus was synthesized.

(ii) Liquid Phase Synthesis of a PRNA Oligomer

A PRNA(Urd) octamer (Boc-isoGln(5'U)$_8$-OH) was produced by the method of Example 2 (11) (compound 15).

(iii) DNA Oligomer-PRNA Oligomer Condensation Reaction

The PRNA(Urd) octamer prepared as described above (Boc-isoGln(5'U)$_8$-OH) (73.8 mg, 3 eq), the BOP reagent (11.1 mg, 3 eq) and HOBt (3.4 mg, 3 eq) were dissolved in DMF (1.5 ml), and the solution was applied to the solid phase carrying the thymidine tetramer. DIEA (2.1 mg, 3.3 eq) was added, in 5 divided portions, to the solid phase, and the treated solid phase was allowed to stand for 3 minutes. After 5 repetitions of this procedure, the solid phase was washed with 7 ml of DMF and further with 7 ml of dichloromethane. Then, 0.5 ml of 28% ammonia water was added to the solid phase and the whole was allowed to stand for 15 minutes to excise the condensate from the solid phase. Thus, a chimeric molecule dodecamer ((PRNA(U)$_8$-DNA (T)$_4$) was obtained. Yield about 50%; m/z (TOP) 4131 (M+2Na)$^{2+}$.

INDUSTRIAL APPLICABILITY

The nucleoside derivatives of the invention are hardly decomposed not only by exonucleases but also endonucleases and can exist in the living bodies for a long period after administration thereto. Further, the nucleoside derivatives of the invention are excellent in affinity for nucleic acids (RNAS, DNAS). Therefore, the nucleoside derivatives of the invention can be prepared as antisense molecules either as such or by introducing into other molecules such as DNAs, RNAs, or derivatives thereof. Furthermore, the nucleoside derivatives of the invention give, in vivo, only degradation products showing no or very slight biological toxicity, such as nucleotides or amino acid derivatives; and, in this sense, too, they are useful as antisense molecules.

Such antisense molecules can control the expression of genes to which the antisense method has been applied. More specifically, they can form double strands with sense-strand RNAs, for instance, to thereby inhibit the formation (translation) of biological components (proteins) causative of diseases, or can form triple strands with double-stranded DNAs to inhibit the transcription thereof into mRNAs. When used as antisense molecules, the nucleoside derivatives of the invention can thus inhibit the functions of target mRNAs/genes and are effective in the treatment of genetic diseases such as cancer and hereditary diseases.

The nucleoside derivatives of the invention are also characterized in that their base moieties can change from anti to syn orientation or from syn to anti orientation under the influence of the occurrence and concentrations of "borates", alkaline earth metals, transition metals or sugars or under the influence of pH, light, temperature and other factors. Therefore, by controlling such conditions, it becomes possible to control their ability to bind to nucleic acid sequences, and they are expected to serve as novel antisense molecules capable of reversibly controlling the on-off of gene function expressions in the antisense method.

What is claimed is:

1. A nucleoside derivative represented by the general formula (1):

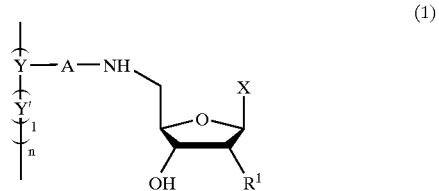

wherein X is(are) the same or different and each represents an optionally substituted pyrimidine nucleic acid base or an optionally substituted purine nucleic acid base, Y and Y' are the same or different and each represents at least one amino acid or amino acid derivative selected from the group consisting of serine, threonine, ornithine, aspartic acid, glutamc acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonyihomoglutamic acid, R$^1$ represents a hydrogen atom or a hydroxyl group, A represents a carbonyl or thiocarbonyl group, 1 is an integer of 0 to 5, and n is an integer of 1 to 100.

2. The nucleoside derivative according to claim 1, wherein, in general formula (1), X is uracil or a derivative thereof represented by the formula (2):

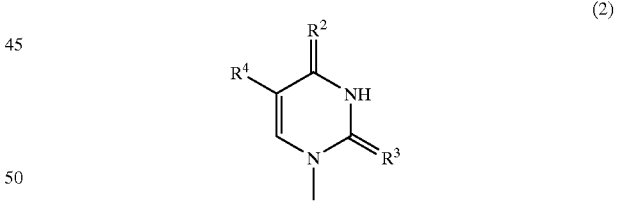

wherein R$^2$ and R$^3$ are the same or different and each represents an oxygen or sulfur atom, and R$^4$ represents a hydrogen or halogen atom or an alkyl, alkenyl or alkynyl group.

3. The nucleotide derivative according to claim 1, wherein, in general formula (1), X is at least one member selected from the group consisting of 5-fluorouracil, 5-bromouracil, 5-iodouracil, 2-thiouracil, 4-thiouracil, 2,4-dithiouracil, 5-methyluracil, 5-vinyluracil, 5-ethynyluracil, 5-fluorocytosine, 5-bromocytosine, 5-iodocytosine, 5-ethylcytosine, hypoxanthine, 8-fluoroguanine, 8-bromoguanine, 8-iodoguanine, 1,N$^6$-ethenoadenine, 8-fluoroadenine, 8-bromoadenine and 8-iodoadenine.

4. A nucleoside derivative represented by the general formula (1):

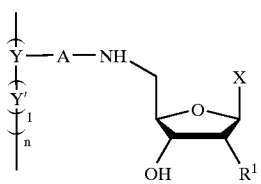

(1)

wherein X is(are) the same or different and each represents an optionally substituted pyrimidine nucleic acid base or an optionally substituted purine nucleic acid base, Y is a group represented by the formula (i):

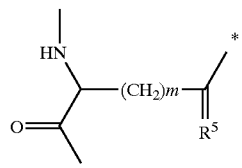

(i)

wherein m is an integer of 1 to 3, $R^5$ represents an oxygen or sulfur atom, and * indicates the site of bonding to A in the nucleoside derivative represented by general formula (1); Y' represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a single bond; l is an integer of 0 to 5 when $R^5$ represents a sulfer atom, l is an integer of 1 to 5 when $R^5$ represents an oxygen atom, and n is an integer of 1 to 100.

5. The nucleoside derivative according to claim 1, wherein, in general formula (1), Y is a group represented by the formula (iii):

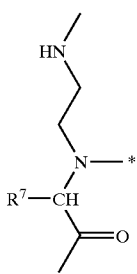

(iii)

wherein $R^7$ represents a hydrogen atom or a carboxymethyl, carboxyethyl, hydroxymethyl, aminobutyl or aminopropyl group, and * indicates the site of bonding to A in the nucleoside derivative represented by general formula (1); here, A represents a carbonyl or thiocarbonyl group.

6. A method for producing the nucleoside derivative as defined in claim 4 which comprises the step 1 of producing a 5'-amino-nucleoside derivative by aminating the 5'-hydroxyl group of a nucleoside or a derivative thereof, the step 2 of producing an amino acid ω-pentachlorophenyl ester derivative by reacting an amino acid, or a derivative thereof represented by the formula:

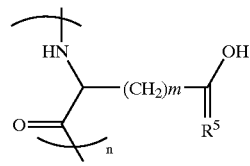

wherein $R^5$ represents an oxygen or sulfur atom, m is an integer of 1 to 3, and n is an integer of 1 to 100 with pentachlorophenyl trichloroacetate, and the step 3 of reacting the 5'-amino-nucleoside derivative and amino acid ω-pentachlorophenyl ester derivative obtained in the step 1 and step 2, respectively, with each other for bonding them together.

7. A method for producing an oligomer or polymer (n=2 to 100) of the nucleoside derivative as defined in claim 5, which comprises the step 1 of producing a nucleoside derivative monomer (n=1) by reacting a 5'-amino-nucleoside derivative with an amino acid or a derivative thereof protected at the N terminus and C terminus as represented by the formula:

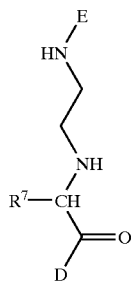

wherein $R^7$ represents a hydrogen atom or a carboxymethyl, carboxyethyl, hydroxymethyl, aminobutyl or aminopropyl group, D represents a carboxyl-protecting group and E represents an amino-protecting group, the step 2 of deprotecting the C terminus of said monomer, the step 3 of deprotecting the N terminus of said monomer, the step 4 of reacting the C-terminus deprotection product obtained in step 2 with the N-terminus deprotection product obtained in step 3 in the manner of condensation, and the step of further repeating the steps 2 to 4 according to need.

8. A nucleoside derivative represented by the general formula (1):

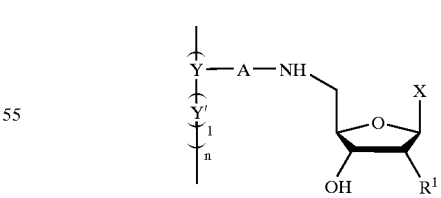

(1)

wherein X is(are) the same or different and each represents an optionally substituted pyrimidine nucleic acid base or an optionally substituted purine nucleic acid base, Y and Y' are the same or different and each represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a single bond, l is an integer of 1 to 5, and n is an integer of 1 to 100.

9. The nucleoside derivative according to claim 8, wherein, in general formula (1), X is uracil or a derivative thereof represented by the formula (2):

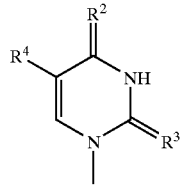

(2)

wherein $R^2$ and $R^3$ are the same or different and each represents an oxygen or sulfur atom, and $R^4$ represents a hydrogen or halogen atom or an alkyl, alkenyl or alkynyl group.

10. The nucleotide derivative according to claim 8, wherein, in general formula (1), X is at least one member selected from the group consisting of 5-fluorouracil, 5-bromouracil, 5-iodouracil, 2-thiouracil, 4-thiouracil, 2,4-dithiouracil, 5-methyluracil, 5-vinyluracil, 5-ethynyluracil, 5-fluorocytosine, 5-bromocytosine, 5-iodocytosine, 5-ethylcytosine, hypoxanthine, 8-fluoroguanine, 8-bromoguanine, 8-iodoguanine, 1,$N^6$-ethenoadenine, 8-fluoroadenine, 8-bromoadenine and 8-iodoadenine.

11. The nucleoside derivatives according to claim 8, wherein, in general formula (1), Y is a group represented by the formula (ii):

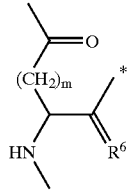

(ii)

wherein m is an integer of 1 to 3, $R^6$ represents an oxygen or sulfur atom, and * indicates the site of bonding to A in the nucleoside derivative represented by general formula (1).

12. An N-protected nucleoside derivative represented by the general formula:

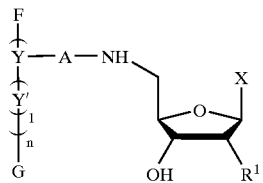

wherein X is(are) the same or different and each represents an optionally substituted pyrimidine nucleic acid base or an optionally substituted purine nucleic acid base, Y and Y' are the same or different and each represents at least one amino acid or amino acid derivative selected from the group consisting of seine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a carbonyl or thiocarbonyl group, F represents a 9-fluorenylcarbonyl group, G represents a hydroxyl group or a benzyl ester group, l is an integer of 0 to 5, and n is 1.

13. An N-protected nucleoside derivative represented by the general formula:

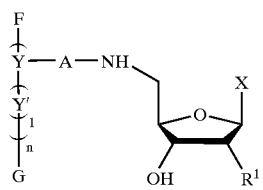

wherein X is(are) the same or different and each represents an optionally substituted pyrimidine nucleic acid base or an optionally substituted purine nucleic acid base, Y is a group represented by the formula (i):

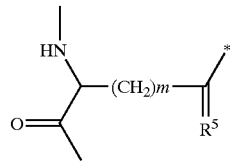

(i)

wherein m is an integer of 1 to 3, $R^5$ represents an oxygen or sulfur atom, and * indicates the site of bonding to A in the nucleoside derivative represented by general formula (1); Y' represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a single bond, F represents a 9-fluorenylcarbonyl group, G represents a hydroxyl group or a benzyl ester group, l is an integer of 0 to 5, and n is 1.

14. An N-protected nucleoside derivative represented by the general formula:

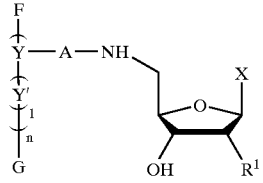

wherein X is(are) the same or different and each represents an optionally substituted pyrimidine nucleic acid base or an optionally substituted purine nucleic acid base, Y and Y' are the same or different and each represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a single bond, F represents a 9-fluorenylcarbonyl group, G represents a hydroxyl group or a benzyl ester group, 1 is an integer of 1 to 5, and n is 1.

15. A solid phase method for producing oligo- or polynucleoside derivatives, comprising:

preparing the N-protected nucleoside derivative according to any one of claims 12, 13 and 14 as a starting monomer;

coupling said N-protected nucleoside derivative to a solid phase;

eliminating the N-protecting group from the solid phase-bound nucleoside derivative; and coupling another N-protected nucleoside derivative to the nucleoside derivative from which N-protecting group has been removed.

16. A method of producing nucleoside derivatives represented by the general formula:

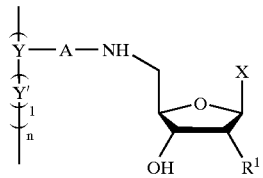

wherein X is(are) the same or different and each represents an optionally substituted pyrimidine nucleic acid base or an optionally substituted purine nucleic acid base, Y and Y' are the same or different and each represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a carbonyl or thiocarbonyl group, 1 is an integer of 0 to 5, and n is an integer of 2 to 100, said method comprising:

preparing the N-protected nucleoside derivative as defined in claim 12 as a starting material;

coupling said N-protected nucleoside derivative to a solid phase;

eliminating the N-protecting group from the solid phase-bound nucleoside derivative; and coupling another N-protected nucleoside derivative to the nucleoside derivative from which N-protecting group has been removed.

17. A method of producing nucleoside derivatives represented by the general formula:

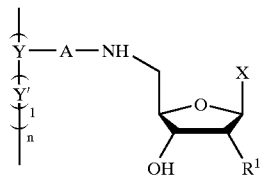

wherein X is(are) the same or different and each represents an optionally substituted pyrimidine nucleic acid base or an optionally substituted purine nucleic acid base, Y is a group represented by the formula (i):

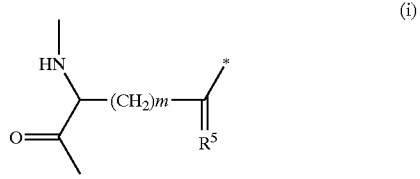

(i)

wherein m is an integer of 1 to 3, $R^5$ represents an oxygen or sulfur atom, and * indicates the site of bonding to A in the nucleoside derivative represented by general formula (1); Y' represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonyihomoglutamic acid, $R^1$ represents a hydrogen atom or a hydroxyl group, A represents a single bond, 1 is an integer of 0 to 5, and n is an integer of 2 to 100, said method comprising:

preparing the N-protected nucleoside derivative as defined in claim 13 as a starting material;

coupling said N-protected nucleoside derivative to a solid phase;

eliminating the N-protecting group from the solid phase-bound nucleoside derivative; and coupling another N-protected nucleoside derivative to the nucleoside derivative from which N-protecting group has been removed.

18. A method of producing nucleoside derivatives represented by the general formula:

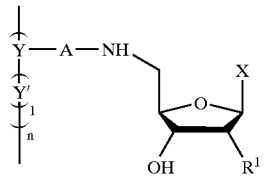

wherein X is(are) the same or different and each represents an optionally substituted pyrimidine nucleic acid base or an optionally substituted purine nucleic acid base, Y and Y' are the same or different and each represents at least one amino acid or amino acid derivative selected from the group consisting of seine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a single bond, 1 is an integer of 1 to 5, and n is an integer of 2 to 100, said method comprising:

preparing the N-protected nucleoside derivative as defined in claim 14 as a starting material coupling said N-protected nucleoside derivative to a solid phase;

eliminating the N-protecting group from the solid phase-bound nucleoside derivative; and coupling another N-protected nucleoside derivative to the nucleoside derivative from which N-protecting group has been removed.

19. The nucleoside derivative according to claim 1, wherein X is(are) a substituted pyrimidine nucleic acid base or substituted purine nucleic acid base selected from the group consisting of halogenated pyrimidine nucleic acid base, halogenated purine nucleic acid base, deaminated pyrimidine nucleic acid base, deaminated purine nucleic acid base, pyrimidine nucleic acid base having a sulfur atom(s) in lieu of an oxygen atom(s) of uracil, cytosine or thymine, purine nucleic acid base having a sulfur atom(s) in lieu of an oxygen atom(s) of adenine or guanine, pyrimidine nucleic acid base substituted by an alkyl, alkenyl or alkynyl group, and purine nucleic acid base substituted by an alkyl, alkenyl or alkynyl group.

20. A nucleoside derivative represented by the general formula (1):

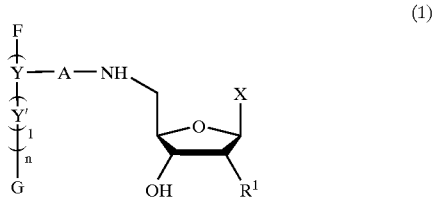

(1)

wherein Y is a group represented by the formula (i):

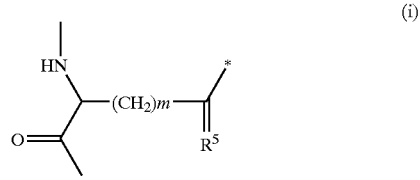

(i)

wherein m is an integer of 1 to 3, $R^5$ represents an oxygen or sulfur atom, and * indicates the site of bonding to A in the nucleoside derivative represented by general formula (1); Y' represents at least one amino acid or amino acid derivative selected from the group consisting of seine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, $R^1$ represents a hydrogen atom or a hydroxyl group, A represents a single bond; 1 is an integer of 0 to 5, n is an integer of 1 to 100, and X is(are) the same or different and each represents a substituted pyrimidine nucleic acid base or substituted purine nucleic acid base selected from the group consisting of halogenated pyrimidine nucleic acid base, halogenated purine nucleic acid base, deaminated pyrimidine nucleic acid base, deaminated purine nucleic acid base, pyrimidine nucleic acid base having a sulfur atom(s) in lieu of an oxygen atom(s) of uracil, cytosine or thymine, purine nucleic acid base having a sulfur atom(s) in lieu of an oxygen atom(s) of adenine or guanine, pyrimidine nucleic acid base substituted by an alkyl, alkenyl or alkynyl group, and purine nucleic acid base substituted by an alkyl, alkenyl or alkynyl group.

21. The nucleoside derivative according to claim 8, wherein X is(are) a substituted pyrimidine nucleic acid base or substituted purine nucleic acid base selected from the group consisting of halogenated pyrimidine nucleic acid base, halogenated purine nucleic acid base, deaminated pyrimidine nucleic acid base, deaminated purine nucleic acid base, pyrimidine nucleic acid base having a sulfur atom(s) in lieu of an oxygen atom(s) of uracil, cytosine or thymine, purine nucleic acid base having a sulfur atom(s) in lieu of an oxygen atom(s) of adenine or guanine, pyrimidine nucleic acid base substituted by an alkyl, alkenyl or alkynyl group, and purine nucleic acid base substituted by an alkyl, alkenyl or alkynyl group.

22. The N-protected nucleoside derivative according to claim 12, wherein X is(are) a substituted pyrimidine nucleic acid base or substituted purine nucleic acid base selected from the group consisting of halogenated pyrimidine nucleic acid base, halogenated purine nucleic acid base, deaminated pyrimidine nucleic acid base, deaminated purine nucleic acid base, pyrimidine nucleic acid base having a sulfur atom(s) in lieu of an oxygen atom(s) of uracil, cytosine or thymine, purine nucleic acid base having a sulfur atom(s) in lieu of an oxygen atom(s) of adenine or guanine, pyrimidine nucleic acid base substituted by an alkyl, alkenyl or alkynyl group, and purine nucleic acid base substituted by an alkyl, alkenyl or alkynyl group.

23. The N-protected nucleoside derivative according to claim 13, wherein X is(are) a substituted pyrimidine nucleic acid base or substituted purine nucleic acid base selected from the group consisting of halogenated pyrimidine nucleic acid base, halogenated purine nucleic acid base, deaminated pyrimidine nucleic acid base, deaminated purine nucleic acid base, pyrimidine nucleic acid base having a sulfur atom(s) in lieu of an oxygen atom(s) of uracil, cytosine or thymine, purine nucleic acid base having a sulfur atom(s) in lieu of an oxygen atom(s) of adenine or guanine, pyrimidine nucleic acid base substituted by an alkyl, alkenyl or alkynyl group, and purine nucleic acid base substituted by an alkyl, alkenyl or alkynyl group.

24. The N-protected nucleoside derivative according to claim 14, wherein X is(are) a substituted pyrimidine nucleic acid base or substituted purine nucleic acid base selected from the group consisting of halogenated pyrimidine nucleic acid base, halogenated purine nucleic acid base, deaminated pyrimidine nucleic acid base, deaminated purine nucleic acid base, pyrimidine nucleic acid base having a sulfur atom(s) in lieu of an oxygen atom(s) of uracil, cytosine or thymine, purine nucleic acid base having a sulfur atom(s) in lieu of an oxygen atom(s) of adenine or guanine, pyrimidine nucleic acid base substituted by an alkyl, alkenyl or alkynyl group, and purine nucleic acid base substituted by an alkyl, alkenyl or alkynyl group.

25. The method according to claim 16, wherein X is(are) a substituted pyrimidine nucleic acid base or substituted purine nucleic acid base selected from the group consisting of halogenated pyrimidine nucleic acid base, halogenated purine nucleic acid base, deaminated pyrimidine nucleic acid base, deaminated purine nucleic acid base, pyrimidine nucleic acid base having a sulfur atom(s) in lieu of an oxygen atom(s) of uracil, cytosine or thymine, purine nucleic acid base having a sulfur atom(s) in lieu of an oxygen atom(s) of adenine or guanine, pyrimidine nucleic acid base substituted by an alkyl, alkenyl or alkynyl group, and purine nucleic acid base substituted by an alkyl, alkenyl or alkynyl group.

26. The method according to claim 17, wherein X is(are) a substituted pyrimidine nucleic acid base or substituted purine nucleic acid base selected from the group consisting of halogenated pyrimidine nucleic acid base, halogenated purine nucleic acid base, deaminated pyrimidine nucleic acid base, deaminated purine nucleic acid base, pyrimidine nucleic acid base having a sulfur atom(s) in lieu of an oxygen atom(s) of uracil, cytosine or thymine, purine nucleic acid base having a sulfur atom(s) in lieu of an oxygen atom(s) of adenine or guanine, pyrimidine nucleic acid base substituted by an alkyl, alkenyl or alkynyl group, and purine nucleic acid base substituted by an alkyl, alkenyl or alkynyl group.

27. The method according to claim 18, wherein X is(are) a substituted pyrimidine nucleic acid base or substituted purine nucleic acid base selected from the group consisting of halogenated pyrimidine nucleic acid base, halogenated purine nucleic acid base, deaminated pyrimidine nucleic acid base, deaminated purine nucleic acid base, pyrimidine nucleic acid base having a sulfur atom(s) in lieu of an oxygen atom(s) of uracil, cytosine or thymine, purine nucleic acid base having a sulfur atom(s) in lieu of an oxygen atom(s) of adenine or guanine, pyrimidine nucleic acid base substituted by an alkyl, alkenyl or alkynyl group, and purine nucleic acid base substituted by an alkyl, alkenyl or alkynyl group.

* * * * *

UNITED STATES PATENT AND TRADEMARK OFFICE
CERTIFICATE OF CORRECTION

PATENT NO.    : 6,872,809 B2
DATED         : March 29, 2005
INVENTOR(S)   : Yoshihisa Inoue and Takehiko Wada It is certified that error appears in the above-identified patent and that said Letters Patent is hereby corrected as shown below:

<u>Title page,</u>
Insert Item -- [30]    Foreign Application Priority Data
              June 13, 2000 (JP) ………….. 2000-177428 --.

Signed and Sealed this

Sixteenth Day of August, 2005

JON W. DUDAS
*Director of the United States Patent and Trademark Office*